(12) United States Patent
Zhang et al.

(10) Patent No.: US 11,250,567 B2
(45) Date of Patent: *Feb. 15, 2022

(54) SYSTEM AND METHOD FOR DETERMINING A BREAST REGION IN A MEDICAL IMAGE

(71) Applicant: SHANGHAI UNITED IMAGING HEALTHCARE CO., LTD., Shanghai (CN)

(72) Inventors: Na Zhang, Shanghai (CN); Juan Feng, Shanghai (CN); Yange Ma, Shanghai (CN); Haihua Zhou, Shanghai (CN); Le Yang, Shanghai (CN); Hao Chen, Shanghai (CN); Wanli Teng, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/859,973

(22) Filed: Apr. 27, 2020

(65) Prior Publication Data
US 2020/0258225 A1 Aug. 13, 2020

Related U.S. Application Data

(63) Continuation of application No. 16/416,577, filed on May 20, 2019, now Pat. No. 10,636,143, which is a (Continued)

(30) Foreign Application Priority Data

Sep. 30, 2015 (CN) .......................... 201510640746.3
Sep. 30, 2015 (CN) .......................... 201510642259.0
Dec. 15, 2015 (CN) .......................... 201510933550.3

(51) Int. Cl.
*G06T 7/00* (2017.01)
*G06T 7/12* (2017.01)
(Continued)

(52) U.S. Cl.
CPC .............. *G06T 7/0012* (2013.01); *G06T 7/11* (2017.01); *G06T 7/12* (2017.01); *G06T 7/136* (2017.01);
(Continued)

(58) Field of Classification Search
CPC ......... G06T 7/0012; G06T 7/12; G06T 7/136; G06T 7/11; G06T 2207/10112;
(Continued)

(56) References Cited

U.S. PATENT DOCUMENTS 5,452,367 A * 9/1995 Bick ...................... G06K 9/342
382/128
5,572,565 A 11/1996 Abdel-Mottaleb
(Continued)

FOREIGN PATENT DOCUMENTS

CN 1924926 A 3/2007
CN 101103924 A 1/2008
(Continued)

OTHER PUBLICATIONS

First Office Action in Chinese Application No. 201510642259.0 dated Jun. 28, 2017, 16 pages.
(Continued)

*Primary Examiner* — Kim Y Vu
*Assistant Examiner* — Molly Delaney
(74) *Attorney, Agent, or Firm* — Metis IP LLC

(57) ABSTRACT

Systems and methods for determining a breast region in a medical image are provided. The methods may include obtaining a first image relating to the breast region, determining a first region including a first plurality of pixels in the
(Continued)

breast region, determining a second region including a second plurality of pixels relating to an edge of the breast region, and determining the breast region by combining the first region and the second region. The second plurality of pixels may include at least a portion of the first plurality of pixels.

19 Claims, 17 Drawing Sheets

Related U.S. Application Data continuation of application No. 15/323,056, filed as application No. PCT/CN2016/101186 on Sep. 30, 2016, now Pat. No. 10,297,024.

(51) Int. Cl.
   *G06T 7/136* (2017.01)
   *G06T 7/11* (2017.01)
   *A61B 6/00* (2006.01)

(52) U.S. Cl.
   CPC ..... *A61B 6/502* (2013.01); *G06T 2207/10112* (2013.01); *G06T 2207/10116* (2013.01); *G06T 2207/20152* (2013.01); *G06T 2207/20221* (2013.01); *G06T 2207/30068* (2013.01)

(58) Field of Classification Search
   CPC .......... G06T 2207/10116; G06T 2207/20152; G06T 2207/20221; G06T 2207/30068; A61B 6/502
   See application file for complete search history.

(56) References Cited

U.S. PATENT DOCUMENTS

| | | | |
|---|---|---|---|
| 5,796,862 A | 8/1998 | Pawlicki | |
| 5,825,910 A | 10/1998 | Vafai | |
| 9,098,935 B2 | 8/2015 | Endo et al. | |
| 10,297,024 B2* | 5/2019 | Yang | G06T 7/12 |
| 10,636,143 B2* | 4/2020 | Zhang | G06T 7/136 |
| 2008/0069421 A1 | 3/2008 | Abramov | |
| 2008/0152220 A1 | 6/2008 | Shi | |
| 2009/0220138 A1 | 9/2009 | Zhang | |
| 2010/0104151 A1 | 4/2010 | Bertens | |
| 2011/0216949 A1* | 9/2011 | Yang | G06T 7/11 382/128 |
| 2014/0355840 A1* | 12/2014 | Pearson Peyton | G06T 7/0014 382/115 |
| 2015/0010219 A1 | 1/2015 | Behiels | |

FOREIGN PATENT DOCUMENTS

| | | |
|---|---|---|
| CN | 101419712 A | 4/2009 |
| CN | 101599174 A | 12/2009 |
| CN | 102956035 A | 3/2013 |
| CN | 103425986 A | 12/2013 |
| CN | 103679685 A | 3/2014 |
| CN | 103700085 A | 4/2014 |
| CN | 103914697 A | 7/2014 |
| CN | 104182965 A | 12/2014 |
| CN | 104574327 A | 4/2015 |
| CN | 104715259 A | 6/2015 |
| CN | 104881858 A | 9/2015 |
| CN | 105701796 A | 6/2016 |
| WO | 2017054775 A1 | 4/2017 |

OTHER PUBLICATIONS

First Office Action in Chinese Application No. 201510640746.3 dated Aug. 2, 2017, 16 pages.
First Office Action in Chinese Application No. 201510933550.3 dated May 4, 2017, 20 pages.
Ng, Hui Fuang et al., An improved method for image thresholding based on the valley-emphasis method, Signal and Information Processing Association Summit and Conference, 2013: 1-4.
Nagi, J. et al., Automated Breast Profile Segmentation for ROI Detection Using Ddigital Mammograms, Biomedical Engineering and Sciences IEEE Xplore, 2010: 87-92.
Mirzaalian, Hengameh et al., Pre-processing Algorithms on Digital Mammograms, IAPR Conference on Machine Vision Applications DBLP, 2007: 118-121.
Wirth, Michael A., Segmentation of the breast region in mammograms using active contours, Proceedings of SPIE—The International Society for Optical Engineering, 2003, 5150: 1995-2006.
Sun, Yajie et al., A Novel Approach for Breast Skin-Line Estimation in Mammograms, IEEE Symposium on Computer-Based Medical Systems IEEE Computer Society, 2005: 241-246.
Li, Yanfeng et al., Pectoral Muscle Segmentation in Mammograms Based on Anatomic Features, Zidonghua Xuebao/acta Automatica Sinica, 2013, 39(8): 1265-1272.
International Search Report in PCT/CN2016/101186 dated Dec. 28, 2016, 4 pages.
Written Opinion of the International Search Authority in PCT/CN2016/101186 dated Dec. 28, 2016, 5 pages.
First Office Action in Chinese Application No. 201680070175.7 dated Jan. 6, 2021, 36 pages.
Sun, Yajie et al., A New Approach for Breast Skin-line Estimation in Mammograms, Pattern Analysis Application, 9:34-47, 2006.
Li, Yanfeng et al., Pectoral Muscle Segmentation in Mammograms Based on Homogenous Texture and Intensity Deviation, Pattern Recognition, 46(3): 681-691, 2013.

* cited by examiner

SYSTEM AND METHOD FOR DETERMINING A BREAST REGION IN A MEDICAL IMAGE

CROSS-REFERENCE TO RELATED APPLICATIONS

This application is continuation of U.S. application Ser. No. 16/416,577, which is continuation of U.S. application Ser. No. 15/323,056, which is a U.S. national stage under 35 U.S.C. § 371 of International Application No. PCT/CN2016/101186, filed on Sep. 30, 2016, designating the United States of America, which claims priority of Chinese Patent Application No. 201510642259.0 filed on Sep. 30, 2015, Chinese Patent Application No. 201510640746.3 filed on Sep. 30, 2015, and Chinese Patent Application No. 201510933550.3 filed on Dec. 15, 2015, the entire contents of each of which are hereby incorporated by reference.

TECHNICAL FIELD

The present disclosure generally relates to image processing, and more particularly, to a system and method for determining a breast region in a medical image.

BACKGROUND

With the development of computer science and information technology, a variety of mammography systems, such as full-field digital mammography (FFDM) system or digital breast tomosynthesis (DBT) system are applied to the screening and/or diagnosis of breast disease.

For an image taken by a mammography system, a computer-aided diagnosis may include the determination of a breast region in an image. The determination of a breast region may allow a detection range of a lesion within the breast region and/or reduce an effect of the background region on the breast region. In image processing, a pectoralis sub-region in the breast region may lead to a lower quality of the image, for example, a lower contrast, non-uniform gray value, etc. Therefore the pectoralis sub-region may need to be identified in the determined breast region.

Accordingly, it would be desirable to effectively determine a breast region in an image and determine a pectoralis sub-region in the breast region.

SUMMARY

The present disclosure provided herein relates to image processing, and more particularly, to a system and method for determining a breast region in a medical image. In an aspect of the present disclosure, a method for determining a breast region in an image is provided. The method may include one or more of the following operations. A first image including a breast region may be acquired, wherein the breast region may include a first region and a second region. The first region including a first plurality of pixels may be determined in the breast region. The second region relating to an edge of the breast region including a second plurality of pixels may be determined based on gray values corresponding to pixels in the first image. The second plurality of pixels may include at least a portion of the first plurality of pixels. The breast region may be determined based on a combination of the first region and the second region.

Another aspect of the present disclosure relates to a system for determining the breast region in the medical image. The system may include an image processing device that is configured to perform the method including one or more of the following operations. A first image including a breast region may be acquired, wherein the breast region may include a first region and a second region. The first region including a first plurality of pixels may be determined in the breast region. The second region relating to an edge of the breast region including a second plurality of pixels may be determined based on gray values corresponding to pixels in the first image. The second plurality of pixels may include at least a portion of the first plurality of pixels. The breast region may be determined based on a combination of the first region and the second region.

In some embodiments, the breast region may be further determined by identifying a pectoralis sub-region in the breast region including one or more of the following operations. A target region including at least portion of the pectoralis sub-region may be determined. A gray value histogram of the target region may be generated. A gray value threshold may be determined based on at least one characteristic of the gray value histogram. The pectoralis sub-region may be determined based on the gray value threshold.

In some embodiments, the characteristic may include a shape of the gray value histogram, a changing rate of the pixel numbers in the gray value histogram, a peak gray value in the gray value histogram, a first-order derivative of the pixel numbers in the gray value histogram, a second-order derivative of pixel numbers in the first gray value histogram, or the like, or a combination thereof.

In some embodiments, the first region in the breast region may be determined based on the Otsu's algorithm.

In some embodiments, the second region relating to an edge of the breast region may be determined based on one or more following operations. A second image may be obtained by performing a first pretreatment on the first image. A third image may be obtained by performing a second pretreatment on the second image, wherein the third image may include the first plurality of pixels corresponding to a first average gray value, the second plurality of pixels corresponding to a second average gray value, and a third plurality of pixels relating to a background region in the third image corresponding to a third average gray value. The first average gray value may be greater than the third average gray value and smaller than the second average gray value. The second region may be determined based on the third image.

In some embodiments, the first pretreatment on the first image may include a gradient transformation or a differential operation. The second pretreatment on the second image may include obtaining a fourth image by performing a negative film operation on the first image and multiplying the second image and the fourth image. The fourth image may be normalized after the negative film operation.

In some embodiments, the first pretreatment on the first image may include a denoising operation. The second pretreatment on the second image may include a gradient transformation or a differential operation. The second image may be obtained by a logarithm transformation on the first image before denoising the first image.

In some embodiments, the second region relating to the edge of the breast region may be determined based on an iterative algorithm or the Otsu's algorithm.

In another aspect of the present disclosure, a method for identifying a pectoralis sub-region in a breast region is provided. An image including a breast region may be acquired. A target region in the breast region may be determined, wherein the target region may include a third region relating to the pectoralis sub-region. A first gray value histogram of the target region may be generated. The first gray value of the gray histogram may include a plurality of gray values in the target region and the number of pixels in the target region having a same gray value of the plurality of gray values. A gray value threshold may be determined based on a characteristic of the first gray value histogram. The third region may be determined based on the gray value threshold.

Another aspect of the present disclosure relates to a system for determining the pectoralis sub-region in the breast region. The system may include an image processing device. The image processing device may be configured to perform the method including one or more of the following operations. An image including a breast region may be acquired. A target region in the breast region may be determined. The target region may include a third region relating to the pectoralis sub-region. A first gray value histogram of the target region may be generated. The first gray value of the gray histogram may include a plurality of gray values in the target region and the number of pixels in the target region having a same gray value of the plurality of gray values. A gray value threshold may be determined based on a characteristic of the first gray value histogram. The third region may be determined based on the gray value threshold.

In some embodiments, a boundary of the target region and a boundary of the third region may be determined. If the boundary of the target region does not intersect with the boundary of the third region, the third region may be designated as the pectoralis sub-region. If the boundary of the target region intersects with the boundary of the third region, the target region may be updated based on the intersection between the boundary of the target region and the boundary of the third region.

In some embodiments, the characteristic of the first gray value histogram may include a shape of the first gray value histogram, a changing rate of the plurality of gray values, a peak gray value in the first gray value histogram, a first-order derivative of the first gray value histogram, or a second-order derivative of the first gray value histogram, or the like, or a combination thereof.

In some embodiments, the gray value threshold determined based on the characteristic of the first gray value histogram may include one or more following operations. A second gray value histogram may be obtained by normalizing the first gray value histogram. The second gray value may include a plurality of gray values and the number of pixels having a same gray value of the plurality of gray values. A first gray value may be identified from the plurality of gray values in the second gray value histogram. The first gray value may be corresponding to a maximum number of pixels having a same gray value in the second gray value histogram. A fifth point may be any one point of a plurality of points within a preset neighborhood of the first gray value on the second gray value histogram. The preset neighborhood may be determined based on a range of gray values of the second gray value histogram. A sixth point may be determined on the second gray value histogram based on the fifth point. The sixth point may be closest to the fifth point.

In some embodiments, a second gray value histogram may be obtained by performing a pretreatment on the first gray value histogram. The pretreatment may be performed based on one or more following operations. A total number of pixels in the first gray value histogram may be determined. A range of gray values of the first gray value histogram may be determined. Then an average pixel number may be determined as being a ratio of the total number of pixels in the first gray value histogram to the range of gray values range of the first gray value histogram. A highest gray value of the first gray value histogram may be identified.

In some embodiments, the gray value threshold may be determined based on a threshold segmentation algorithm, for example, an iterative algorithm, the Otsu's algorithm, or the like, or a combination thereof.

In some embodiments, the target region may be determined based on one or more following operations. A first point may be selected on a first boundary of the image (e.g., a horizontal boundary of the image). A second point may be determined based on a first part of an edge of the breast region based on a slope of a first line connecting the first point and the second point. A third point may be determined based on the second point. A distance from the third point to the first boundary may be smaller than a distance from the second point to the first boundary. A fourth point may be determined on a second part of the edge of the breast region based on a slope of a second line connecting the third point and the fourth point. The target region may be determined based on the second line. The target region may be a region grouped by the second line, the first boundary of the image and a second boundary of the image (e.g., a vertical boundary of the image).

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

Figure 1A:
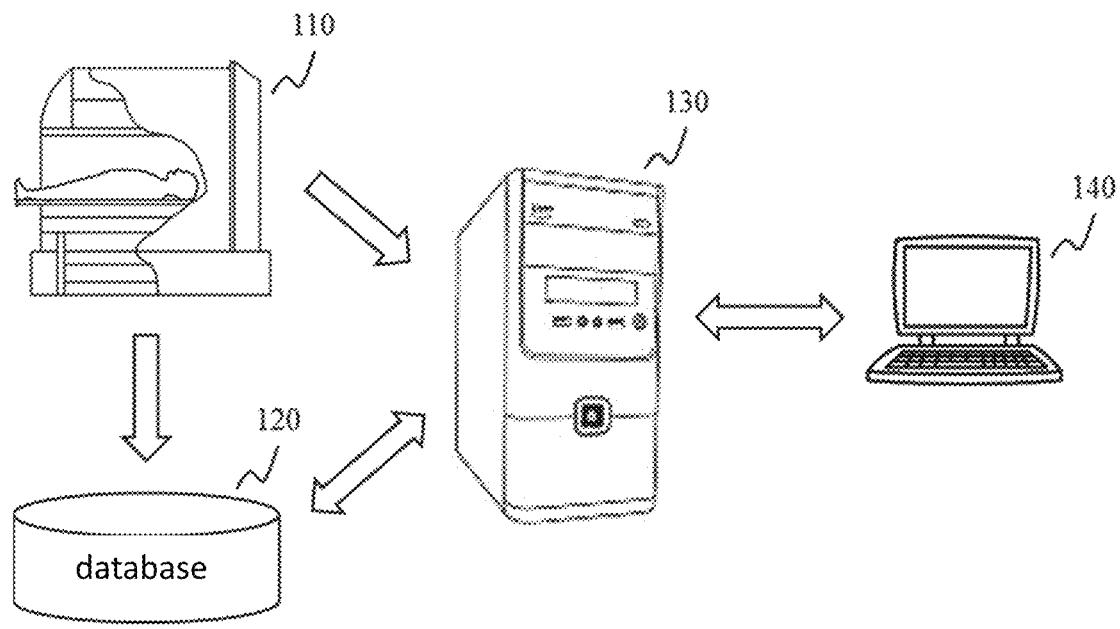
FIG. 1A is a block diagram of a mammography system 100 according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

In some embodiments, in an imaging process, an image including at least one region may be identified based on an image segmentation. An image segmentation (or may be referred to as "recognition," "classification," "extraction," etc.) may be performed to establish a subject model by dividing or partitioning an image into at least one constituent region. The image may be a medical image. The image may be generated and processed via a mammography system. In some embodiments, the image may include a 2D image and/or a 3D image. In the 2D image, its tiniest distinguishable element may be termed as a pixel. In the 3D medical image, its tiniest distinguishable element may be termed as a voxel (or "a volumetric pixel," "a volume pixel"). In some embodiments, the 3D image may also include a series of 2D slices or 2D layers.

The segmentation process may be performed by recognizing one or more characteristics or features of one or more pixels and/or voxels in the image. In some embodiments, exemplary characteristics or features may include gray level, mean gray level, gray value, texture, color, contrast, brightness, or the like, or any combination thereof. In some embodiments, a spatial property of a pixel and/or voxel may also be considered in a segmentation process.

For illustration purposes, the following description is provided to help better understanding an imaging process. It is understood that this is not intended to limit the scope the present disclosure. For persons having ordinary skills in the art, a certain amount of variations, changes and/or modifications may be deducted under guidance of the present disclosure. Those variations, changes and/or modifications do not depart from the scope of the present disclosure.

FIG. 1A is a block diagram of a mammography system 100 according to some embodiments of the present disclosure. It should be noted that the mammography system 100 described below is merely provided for illustration purposes, and not intended to limit the scope of the present disclosure. In some embodiments, the system 100 may be an X-ray mammography (XRM) system. Exemplary X-ray mammography system may include a breast dry plate X-ray photography system, a film-screen mammography system, a digital radiography (DR) system (e.g. a full-field digital mammography (FFDM), a digital breast tomosynthesis (DBT) system, a phase contrast mammography (PCM) system, a computed radiography (CR) system, a multi-modality system, or the like, or a combination thereof.

As illustrated in FIG. 1A, the mammography system 100 may include an imaging device 110, a database 120, an image processing device 130, and an external device 140.

The imaging device 110 may generate or provide an image via scanning a subject, or a part of the subject. The image may be a medical image that may be transmitted to the image processing device 130 to be processed, or stored in the database 120. The image may be two-dimensional (2D) or three-dimensional (3D). The image format may include joint photographic experts group (JPEG), tagged medical image file format (TIFF), graphics interchange format (GIF), kodak flash pix (FPX), digital imaging and communications in medicine (DICOM).

The imaging device 110 may utilize a technique including, for example, a breast dry plate X-ray photography, a film-screen mammography, a digital radiography (DR) (e.g. a full-field digital mammography (FFDM), a digital breast tomosynthesis (DBT), a phase contrast mammography (PCM), etc.), a computed radiography (CR), a multi-modality, or the like, or a combination thereof. In some embodiments, the imaging device 110 may be a multi-modality, for example, a full-field digital mammography digital breast tomosynthesis (FFDM-DBT) device.

The database 120 may store an image and/or relevant information of an image. The relevant information of the image may include an algorithm to process the image, a model related to a patient, or the like, or a combination thereof. The database 120 may be a hierarchical database, a network database, a relational database, or the like, or a combination thereof. The database 120 may also store the operational parameters related with the mammography system 100. The database 120 may be local, or remote. In some embodiments, the database 120 may be a storage device that stores information with electric energy, such as a random access memory (RAM), a read only memory (ROM), or the like, or a combination thereof. The random access memory (RAM) may include a dekatron, aselectron, a delay line memory, a williams tube, a dynamic random access memory (DRAM), a static random access memory (SRAM), thyristor random access memory (T-RAM), zero capacitor random access memory (Z-RAM) or a combination thereof. The read only memory (ROM) may include a read-only memory bubble memory, a magnetic button line memory, a memory thin film, a magnetic plate line memory, a core memory, a magnetic drum memory, a CD-ROM drive, hard disk, magnetic tape, nonvolatile memory early (the NVRAM), a phase change memory, a magnetoresistive random access memory modules, a ferroelectric random access memory, a nonvolatile SRAM, a flash memory, a type of electronic erasing rewritable read-only memory, an erasable programmable read-only memory, a programmable read-only memory, a mask ROM, a floating connecting doors random access memory, a nano random access memory, a racetrack memory, a variable resistive memory, a programmable metallization cell and the like, or a combination thereof. In some embodiments, the database 120 may be a storage device that stores information with magnetic energy such as hard disk, floppy disk, magnetic tape, magnetic core memory, bubble memory, U disk, flash memory or the like, or a combination thereof. In some embodiments, the database 120 may be a storage device that store information with optics energy such as a CD, DVD, or the like, or a combination thereof.

In some embodiments, the database 120 may be a part of the mammography system 100. In some embodiments, the database 120 may be a part of the image processing device 130. In some embodiments, the database 120 may connect to other components in the mammography system 100 via a network. As an example, the database 120 may communicate with other components in the mammography system 100 via a wired connection, a wireless connection, or a combination thereof.

The image processing device 130 may acquire an image generated via the imaging device 110 or stored in the database 120. The image processing device 130 may process the image and transmit the processed image to the terminal device 140.

In some embodiments, the image processing device 130 may include a processor, a processing core, a memory, or the like, or a combination thereof. For example, the image processing device 130 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a processor, a microprocessor, an advanced RISC machines processor (ARM), or the like, or a combinations thereof.

The terminal device 140 may communicate with the imaging device 110, the image processing device 130, and/or the database 120. In some embodiments, the terminal device 140 may obtain a processed image from the processing device 130. In some embodiments, the terminal device 140 may obtain an image acquired via the imaging device 110 and transmit the image to the processing device 130 to be processed. The terminal device 140 may include an input device, a control panel (not shown in the figure), etc. The input device may be a keyboard, a touch screen, a mouse, a remote controller, or the like, or any combination thereof. An input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be communicated to the processing device 130 via, for example, a bus, for further processing. Other types of the input device may include a cursor control device, such as a mouse, a trackball, or cursor direction keys, etc.

The mammography system 100 may be connected to a network (not shown in the figure). The network may be a local area network (LAN), a wide area network (WAN), a public network, private network, a proprietary network, a public switched telephone network (PSTN), the Internet, virtual networks, metropolitan area networks, telephone networks or the like, or a combination thereof. In some embodiments, the mammography system 100 may be a full-field digital mammography (FFDM) system or a digital breast tomosynthesis (DBT) system. The network may be a wireless network (Bluetooth, WLAN, Wi-Fi, WiMax, etc.), mobile networks (2G, 3G, 4G signals, etc.), or other connections (virtual private network (VPN), a shared network, near field communication (NFC, ZigBee, etc.). In some embodiments, the communication among the imaging device 110, the image processing device 130, the database 120, and the terminal device 140 may be achieved via a wired connection or a wireless connection, or a combination thereof.

The image processing device 130 and/or the database 140 may perform a function in the mammography system 100 via a cloud computing platform. The cloud computing platform may include a storage-based type cloud platform, a handle data-based computing cloud platform, and an integrated cloud computing platform. The cloud platform configured in the mammography system 100 may be a public cloud, a private cloud, or a hybrid cloud, or the like, or a combination thereof. For example, according to actual needs, some image information and/or data information generated in the mammography system 110 may be calculated and/or stored by the cloud platform. Other image information and/or data information may be calculated and/or stored by the image processing device 130 and/or database 120.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the database 120 may be a data storage including cloud computing platforms, such as, public cloud, private cloud, community and hybrid clouds, etc. However, those variations and modifications do not depart the scope of the present disclosure.

Figure 1B:
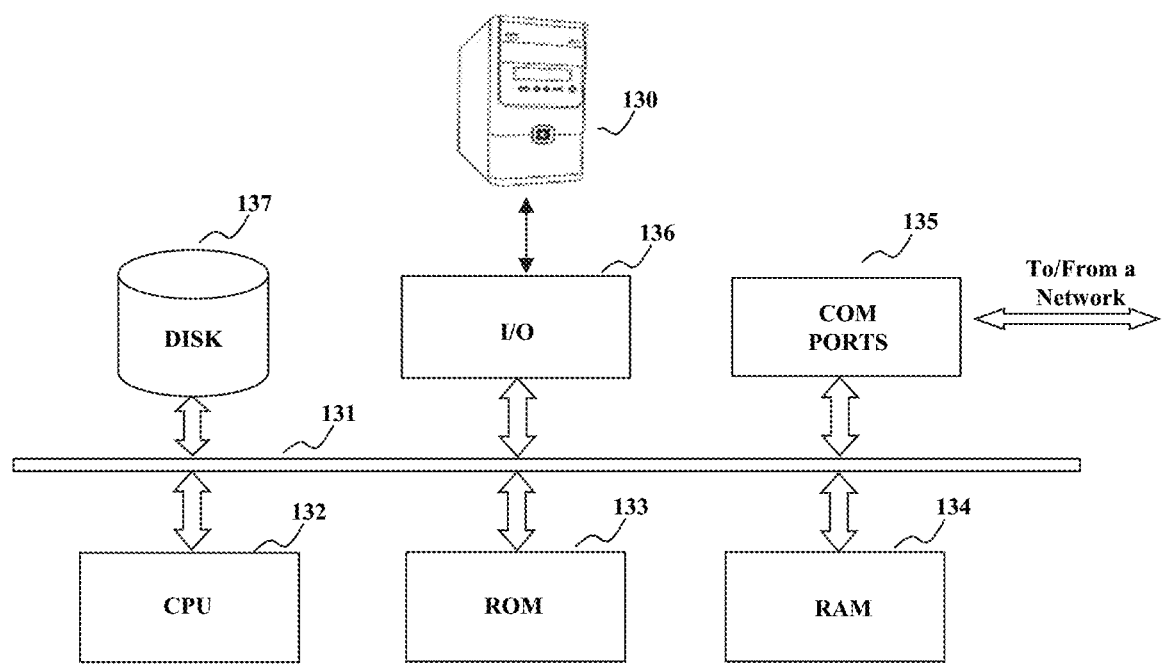
FIG. 1B illustrates an exemplary architecture of a computer on which the image processing device 130, or a portion thereof, may be implemented according to some embodiments of the present disclosure.

FIG. 1B illustrates an exemplary architecture of a computer on which the image processing device 130, or a portion thereof, may be implemented according to some embodiments of the present disclosure. The image processing device 130, or a portion thereof, may be implemented on a computer via its hardware, software program, firmware, or a combination thereof. Although only one such computer is shown, for convenience, the computer functions relating to the image processing device 130 as described herein may be implemented in a distributed fashion on a number of similar platforms, to distribute the processing load.

The image processing device 130, for example, may include a COM ports 135 connected to and from a network connected thereto to facilitate data communications. The image processing device 130 may also include a central processing unit (CPU) 132, in the form of one or more processors, for executing program instructions. The exemplary computer platform may include an internal communication bus 131, a program storage and data storage of different forms, e.g., a disk 137, a read only memory (ROM) 133, or a random access memory (RAM) 134, for various data files to be processed and/or communicated by the computer, as well as possibly program instructions to be executed by the CPU 132. The image processing device 130 may also include an I/O port 136, supporting input/output flows between the image processing device and other components therein such as the terminal device 140. The image processing device 130 may also receive programming and data via network communications.

Hence, aspects of the methods of the image processing and/or other processes, as outlined herein, may be embodied in programming. Program aspects of the technology may be thought of as "products" or "articles of manufacture" typically in the form of executable code and/or associated data that is carried on or embodied in a type of machine readable medium. Tangible non-transitory "storage" type media may include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a mammography system into the hardware platform(s) of a computing environment or other system implementing a computing environment or similar functionalities in connection with the image processing. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms including, for example, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media may include dynamic memory, such as a main memory of such a computer platform. Tangible transmission media may include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore may include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described herein may be embodied in a hardware device, it may also be implemented as a software only solution, e.g., an installation on an existing server. In addition, the image processing device as disclosed herein may be implemented as a firmware, firmware/software combination, firmware/hardware combination, or a hardware/firmware/software combination.

Figure 2:
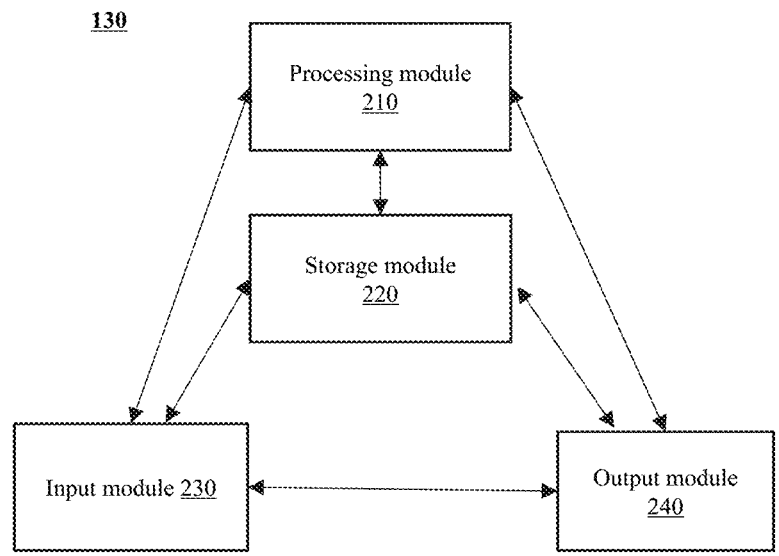
FIG. 2 illustrates an exemplary block diagram of the image processing device 130 according to some embodiments of the present disclosure.

FIG. 2 illustrates an exemplary block diagram of the image processing device 130 according to some embodiments of the present disclosure. As shown in FIG. 2, the image processing device 130 may include a processing module 210, a storage module 220, an input module 230, and an output module 240. The different modules in the image processing device 130 may communicate with each other via a wireless connection or a wired connection, or a combination thereof. As an example, the wired connection may include the internal communication bus 131. As another example, the different modules may connected to and from a network to facilitate data communications via the COM ports 135 as illustrated in FIG. 1B. The image processing device 130 may be integrated with the imaging device 110, or independent from but configured to communicate with the imaging device 110, as described elsewhere in the present disclosure.

The processing module 210 may perform various treatments on an image. In some embodiments, the processing module 210 may perform various treatments via the CPU 132 in FIG. 1B. In some embodiments, the processing module 210 may include one of more processing units, e.g., a graphics processor unit (GPU), a digital signal processor (DSP), a system on a chip (SoC), a microcontroller unit (MCU), or the like, or a combination thereof.

The image may be obtained directly from the storage module 220, or may be obtained from an external device, e.g., the imaging device 110 or the database 120 via the input module 230. In some embodiments, the image may be a medical image, including, a full-field digital mammography (FFDM) image, a digital breast tomosynthesis (DBT) image, a phase contrast mammography (PCM) image, a computed radiography (CR) image, a multi-modality image, or the like, or a combination thereof. The treatment may include a gray value histogram processing, a normalization operation, a geometric transformation, a spatial transformation, a smooth processing, an image enhancement, an image segmentation, an image transformation, an image restoration, an image compression, a feature extraction, or the like, or a combination thereof.

As an example, the processing module 210 may enhance a specific area in an image via an image enhancement treatment. The image enhancement treatment may be based on a Logarithmic transformation, a Gamma transformation, a histogram equalization, a Pseudo-color enhancement, a filtering, a gradient operator, or the like, or a combination thereof.

As another example, the processing module 210 may extract a specific region of an image via a segmentation technique. The segmentation technique may include a region-based segmentation, an edge-based segmentation, a wavelet transform segmentation, a mathematical morphology segmentation, an artificial neural network-based segmentation, a genetic algorithm-based segmentation, or the like, or a combination thereof. The region-based segmentation may base on a threshold segmentation algorithm, cluster analysis, region growing, or the like, or a combination thereof. The threshold segmentation algorithm may include global threshold algorithm (e.g. P-quantile algorithm, an iterative algorithm, concave histogram analysis, the Otsu's algorithm, a fuzzy set algorithm, a two-dimensional entropy thresholding algorithm, a histograms threshold technique, a relaxation algorithm, etc.), a local threshold algorithm, and a multi-threshold algorithm (e.g. a wavelet-based multi-threshold algorithm, a boundary-point-based recursive multi-threshold algorithm, etc.), or the like, or a combination thereof. The cluster analysis may include a K-means algorithm, a fuzzy C-means clustering (FCM) algorithm, etc. The mathematical morphology segmentation may be based on a Hysen points enhanced model, a Hysen line enhanced model, a multiscale Gaussian template matching model, a multi-scale morphological filtering model, etc. The edge-based segmentation may be based on a differential operator (e.g. the Robert operator, the Sobel operator, the Prewitt operator, the Log operator, the Canny operator, etc.), a surface-based fitting, a boundary and surface-based fitting, a serial boundary searching, or the like, or a combination thereof.

The storage module 220 may store data relating to the mammography system 100. The data stored may be a numerical value, an image, information of a subject, an instruction and/or a signal to operate the processing module 210, a voice, a model relating to a patient, an algorithm relating to an image processing method, or the like, or a combination thereof. In some embodiments, the numerical value may include a threshold, a CT value, the number of iterations, or the like, or any combination thereof. The algorithm may include a series of image processing methods. The image may include a raw image or a processed image (e.g., an image after pretreatment). The model relating to a patient may include the background information of the patient, such as, ethnicity, citizenship, religion, gender, age, matrimony state, height, weight, medical history (e.g., history relating to different organs, or tissues), job, personal habits, or the like, or a combination thereof. In some embodiments, the storage module 220 may output information to the output module 240 and/or the processing module 210.

The storage module 220 may include a random access memory (RAM), a read only memory (ROM), for example, a hard disk, a floppy disk, a cloud storage, a magnetic tape, a compact disk, a removable storage, a dynamic random access memory (DRAM), a static random access memory (SRAM), a bubble memory, a thin film memory, a magnetic plated wire memory, phase change memory, a flash memory, or the like, or a combination thereof. In some embodiments, the storage module 220 may be a removable storage such as a U flash disk that may read data from and/or write data to the processing module 210 in a certain manner. As an example, the storage module 220 may perform a function of storing data via the disk 137, the read only memory (ROM) 133, or the random access memory (RAM 134) in FIG. 1B. The storage module 130 may also include other similar means for providing computer programs or other instructions to the computer. In some embodiments, the storage module 220 may be operationally connected with one or more virtual storage resources (e.g., cloud storage, a virtual private network, other virtual storage resources, etc.).

The input module 230 may acquire, for example, a medical image from the imaging device 110, the database 120, or the terminal device 140. In some embodiments, the medical image acquired by the input module 230 may be processed in the processing module 210, or stored in the storage module 220. The output module 240 may transmit an image processed by the processing module 210 to the database 120, or the terminal device 140. In some embodiments, the input module 230 and the output module 240 may include an interface including a display, a keyboard, a mouse, a touch screen, a microphone, a sensor, a wireless communication unit or the like, or any combination thereof. In some embodiments, the input module 230 and the output module 240 may input/output flows between the image processing device 130 and other components therein such as the terminal device 140 via the I/O port 136 illustrated in FIG. 1B.

It should be appreciated that the image processing device 130 shown in FIG. 2 may be implemented in various ways. In some embodiments, the image processing device 130 may be implemented by a hardware, a software, or a combination of software and hardware. In some embodiments, the modules may by implemented by a hardware circuit of a programmable hardware device including a super LSI, a gate array, semiconductor logic chips, transistors, a field programmable gate array, programmable logic devices or the like, or a combination thereof. In some embodiments, the modules may by implemented by a software. The software portion may be stored in the database 120, the storage module 220, or a memory system. The software portion may be implemented by an instruction execution unit, e.g., a microprocessor or a dedicated hardware. Those skilled in the art may understand that the above-described method and system may be implemented by computer-executable instructions and/or processor control code, provided by a disk, CD or DVD-ROM, a read-only memory (Firmware) programmable memory or on a data carrier such as optical or electrical signal carrier.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the storage module 220 may be integrated into the processing module 210. In some embodiments, the input module 230 and the output module 250 may be omitted from the system. In some embodiments, the input module 230 and the output module 240 may be integrated into one module. In some embodiments, the image processing device 130 may include a controller module, and the controller module may control modules in the image processing device 130 to acquire, process, store, or output an image.

Figure 3:
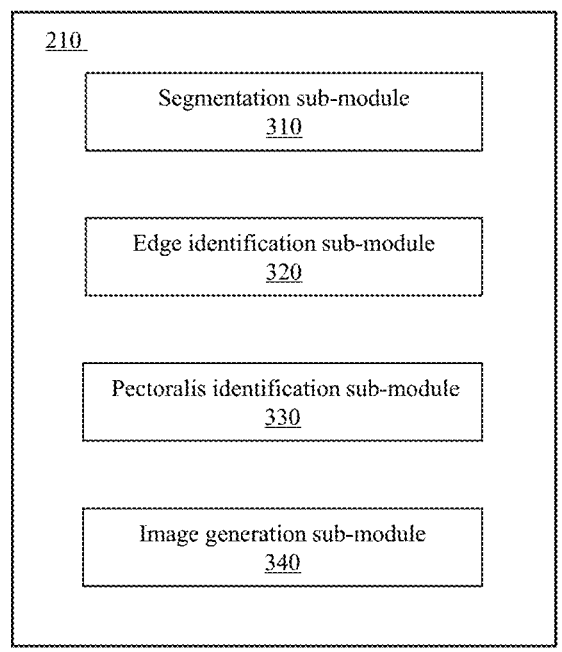
FIG. 3 illustrates an exemplary block diagram of the processing module 210 according to some embodiments of the present disclosure.

FIG. 3 illustrates an exemplary block diagram of the processing module 210 according to some embodiments of the present disclosure. The processing module 210 may include a segmentation sub-module 310, an edge identification sub-module 320, a pectoralis identification sub-module 330, and an image generation sub-module 340. Each sub-module in the processing module 210 may communicate with each other via a wired connection or a wireless connection, or a combination thereof.

The segmentation sub-module 310 may determine a first region in an image. The first region may include at least a portion of a breast region. In some embodiments, the image may be a medical image as described elsewhere in the disclosure. The image may be generated by scanning a subject (e.g., a breast) by the imaging device 110. In some embodiments, the image may be obtained from the database 120 or the terminal device 140 via the input module 230. In some embodiments, the image may be obtained from the storage module 220.

The segmentation sub-module 310 may determine the first region based on a segmentation technique as described elsewhere in the disclosure.

In some embodiments, the segmentation sub-module 310 may perform a pretreatment on the image before segmenting the first region such that the first region is distinguishable from other regions in the image. Merely by way of example, the pretreatment may include a process of geometrical transformation, a process of image enhancing, a process of image smoothing, a normalization operation, or the like, or a combination thereof. The geometrical transformation may include a zooming operation, a translation operation, a mirror operation, a revolve operation, or the like, or a combination thereof. Specifically, the image smoothing operation may be performed based on a Gaussian filter, an average filter, a median filter, a wavelet transformation, or the like, or a combination thereof. The enhancing operation may include a histogram equalization, an image sharpening, a Fourier transform, a high-pass filtering, a low-pass filtering, or the like, or a combination thereof.

The edge identification sub-module 320 may determine a second region in the image. In some embodiments, the second region may be an edge of a breast region. Specifically, the segmentation sub-module 310 and the edge identification sub-module 320 may determine different regions relating to a same subject (e.g., the breast). For example, the segmentation sub-module 310 may determine a general region of the subject. As used herein, the general region of the subject may represent a rough outline of the subject. The edge identification sub-module 320 may determine the edge region (e.g., a region surrounding the edge) of the subject. In some embodiments, the different regions relating to the same subject may at least partially overlap with each other.

In some embodiments, the edge identification sub-module 320 may identify and extract the second region based on a segmentation technique as described elsewhere in the disclosure.

In some embodiments, the edge identification sub-module 320 may perform a pretreatment on the image before identifying the second region. By way of the pretreatment on the image, the gray value of pixels in the image may be adjusted such that the second region is distinguishable from other regions (e.g., the first region determined by way of segmentation by the segmentation sub-module 310) in the image. In some embodiments, the pretreatment may include a point operation, a logical operation, an algebra operation, or the like, or a combination thereof. A point operation may transform the gray value of pixels by a gradient transformation, a negative film operation, a logarithm transformation, a normalization operation, a Gamma transformation, or the like, or a combination thereof. The logical operation may include an AND operation, an OR operation, a NOT operation, or a like, or a combination thereof. The algebra operation may include an addition operation, a subtraction operation, a multiplication operation, a division operation, etc.

The pectoralis identification sub-module 330 may determine a pectoralis sub-region (or referred to as the "third region") in a breast region. In some embodiments, the third region may be identified and segmented based on the breast region determined by the segmentation sub-module 310 and the edge identification sub-module 320. In some embodiments, the pectoralis identification sub-module 330 may determine the pectoralis sub-region based on a segmentation technique as described elsewhere in the disclosure.

In some embodiments, the pectoralis identification sub-module 330 may determine a target region in the breast region. The target region may include at least a portion of the pectoralis sub-region. In some embodiments, the target region may be determined based on a characteristic of the pectoralis sub-region, such as the shape of the pectoralis sub-region, the size of the pectoralis sub-region, the position of the pectoralis sub-region, the structure of the pectoralis sub-region, or the like, or a combination thereof.

In some embodiments, the pectoralis identification sub-module 330 may calculate a gray value histogram of pixels in the target region, and the pectoralis sub-region may be extracted based on a characteristic of the gray value histogram. The gray value histogram may include a plurality of gray values in the target region and a number of pixels in the target region having a same gray value of the plurality of gray value. In some embodiments, the characteristic may include a shape of the gray value histogram, a changing rate of the pixel numbers s in the gray value histogram, a peak gray value in the gray value histogram, a first-order derivative of the gray value histogram, or a second-order derivative of the gray value histogram, or the like, or a combination thereof.

The image generation sub-module 340 may generate an image including, for example, a breast region, based on the first region, the second region, and/or the pectoralis sub-region as described above. In some embodiments, the breast region may be formed by combining the first region and the second region. Furthermore, the breast region may be formed by removing the pectoralis sub-region or substituting the pectoralis sub-region with one or more other regions.

In some embodiments, the image generation sub-module 340 may generate the image including a breast region based on the point operation, the logical operation, the algebra operation, or the like, or a combination thereof, as described elsewhere in the disclosure.

In some embodiments, an image including the breast region generated by the image generation sub-module 340 may be a binary image. As used herein, a binary image may denote that the gray value of pixels in the binary image may be "1" or "0." The value "1" may be represented in white, and the value "0" may be represented in black.

The description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the segmentation sub-module 310 may be integrated into the edge identification sub-module 320. The image generation sub-module 340 may be omitted.

Figure 4:
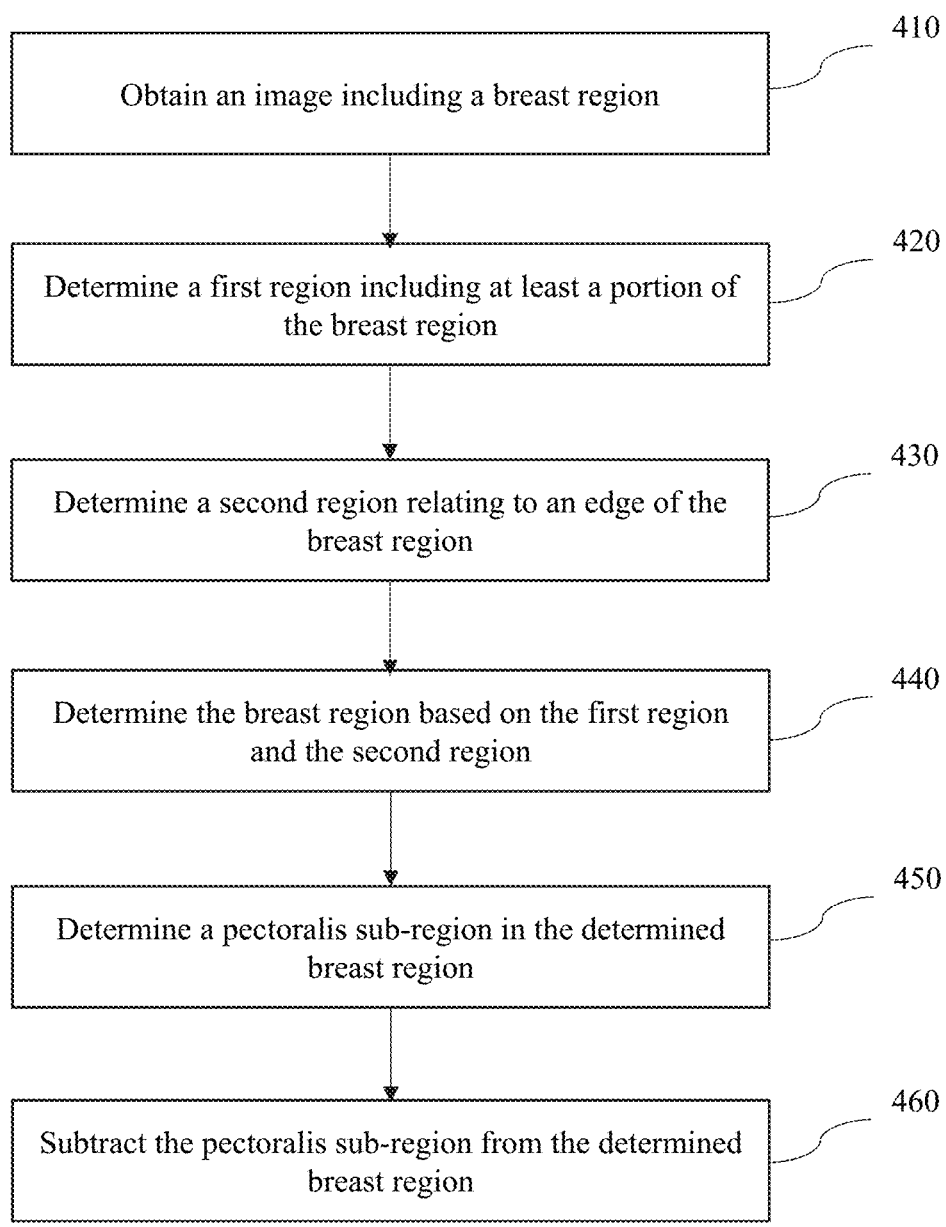
FIG. 4 is a flowchart illustrating a process 400 for determining a breast region according to some embodiments of the present disclosure.

FIG. 4 is a flowchart illustrating a process 400 for determining a breast region according to some embodiments of the present disclosure. In some embodiments, the process may be performed by the image processing device 210.

In 410, an image including a breast region may be obtained. In some embodiments, the image may be a medical image as described elsewhere in the disclosure.

In 420, a first region including at least a portion of the breast region may be determined. The 420 may be performed by the segmentation sub-module 310. In some embodiments, the first region may include a plurality of pixels that may be grouped according to similarity in one or more characteristics of the pixels. For example, the first region may be determined based on the gray values of pixels in the first region. In some embodiments, the gray values of pixels in the first region may change continuously or gradually. The first region in the breast region may be obtained based on a threshold segmentation algorithm. For illustrative purposes, the threshold segmentation algorithm may include comparing the gray value of each pixel in the image with a gray value threshold. If the gray value of one pixel is smaller than the gray value threshold, the pixel may be grouped into the first region. Furthermore, the image may be turned into a binary image with two classes of gray values, by setting, for example, "1" for the pixels belonging to the first region and "0" for the pixels belonging to one or more other regions.

In 430, a second region relating to an edge of the breast region may be determined. The 430 may be performed by the edge identification sub-module 320. In some embodiments, the first region may include a plurality of pixels that are grouped according to the similarity in one or more characteristics of the pixels. In some embodiments, the gray values of pixels in the second region may change sharply from each other. In some embodiments, the second region may be determined according to a changing rate of the gray values of pixels.

For example, the second region may be determined based on an edge detection relating to the changing rate of the gray values of pixels. The edge detection may include a search-based algorithm and/or a zero-crossing based algorithm. The search-based algorithm may detect edges by assessing an edge strength, such as the gradient magnitude via a first-order derivative expression, and searching for a local directional maxima of the gradient magnitude using an estimate of the local orientation of the edge, such as the gradient direction. In some embodiments, the operation of the first-order derivative of gray values of pixels in the second region may be performed by a Roberts Cross operator, a Prewitt operator, a Sobel operator, a Kirsch operator, a Compass operator, or the like, or a combination thereof. The zero-crossing based algorithm may search for zero crossings in a second-order derivative of gray values of pixels in the second region to find the edge. In some embodiments, the operation of the second-order derivative expression may be performed by a Marr-Hildreth operator, a Canny operator, a Laplacian operator, or the like, or a combination thereof.

In some embodiments, the determination of the first region and the second region may be achieved by a same algorithm. As an example, the first region and the second region may be identified based on the Otsu's algorithm. According to the Otsu's algorithm, an adaptive threshold may be applied, and an optimum threshold may be determined to separate the two classes of pixels. Different segmentation thresholds may correspond to different intra-class variance between the foreground pixels and the background pixels. The intra-class variance may denote a dispersion degree between the gray value of the foreground pixels and the background pixels. The larger the intra-class variance between the foreground pixels and the background pixels is, the larger difference between the foreground pixels and the background pixels is. When some parts of the foreground pixels is classified to the background pixels, the intra-class variance may diminish. Accordingly, the segmentation threshold that may lead to a maximum intra-class variance may be deemed the optimum threshold between the foreground pixels and the background pixels.

In some embodiments, the determination of the first region and the second region may be realized by different algorithm. As an example, the first region may be identified by the Otsu's algorithm, and the second region may be identified based on an iterative algorithm. During an iteration, a subsequent segmentation threshold may be determined based on the foreground pixels and the background pixels segmented based on the prior segmentation threshold. If the difference between two segmentation thresholds is smaller than a value (e.g., a present value), the subsequent segmentation threshold may be set as an optimal segmentation threshold and the iteration may be over. Otherwise, if the difference between two segmentation thresholds is equal to or exceeds a value (e.g., a present value), the subsequent segmentation threshold may update the prior segmentation threshold for use in a next iteration.

In 440, the breast region may be determined based on the first region and the second region. The 440 may be performed by the image generation sub-module 340. In some embodiments, the breast region may be obtained based on an addition operation between pixels in the first region and pixels in the second region. In some embodiments, the first region may contain the second region. In some embodiments, the first region may overlap with a portion of the second region. In some embodiments, the first region may not overlap with the second region. In some embodiments, an isolated region including at least one pixel may be identified within the non-overlapped region.

In some embodiments, the isolated region in the breast region may be identified. The pixels in the isolated region may be different from the pixels surrounding the isolated region in the breast region. In some embodiments, the isolated region may be identified and removed based on the gray values of pixels in the isolated region and pixels in one or more regions surrounding the isolated region. For example, the gray values of pixels in the isolated region may be different from the gray values of the pixels surrounding the isolated region. The isolated region may include a set of pixels with a gray value of "0" in the breast region, while the gray values of pixels surrounding the isolated region may be "1," then the gray values of pixels in the isolated region may be identified and changed to "1."

In 450, a pectoralis sub-region may be determined in the breast region. The 450 may be performed by the pectoralis identification sub-module 330. In some embodiments, the determination of the pectoralis sub-region may be based on a same algorithm as the determination of the first region or the determination of the second region. As an example, the first region and the pectoralis sub-region may both be identified based on the Otsu's algorithm. In some embodiments, the determination of the pectoralis sub-region may be based on an algorithm different from the determination of the first region or the determination of the second region. As an example, the first region or the second region may be identified based on the Otsu's algorithm, while the pectoralis sub-region may be identified based on an iterative algorithm. Details regarding the determination of the pectoralis sub-region may be found elsewhere in the present disclosure. See, for example, FIG. 10 and the description thereof.

In 460, the determined pectoralis sub-region may be subtracted from the breast region. In some embodiments, the pectoralis sub-region may be subtracted from the determined breast region based on a subtraction operation between the pixels in the pectoralis sub-region and the pixels in the determined breast region.

It should be noted that the flowchart depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the 420 and the 430 may be performed simultaneously. In some embodiments, the 420 and/or the 430 may include a pretreatment on the image including suppressing, weakening and/or removing a detail, a mutation, a noise, or the like, or any combination thereof.

Figure 5:
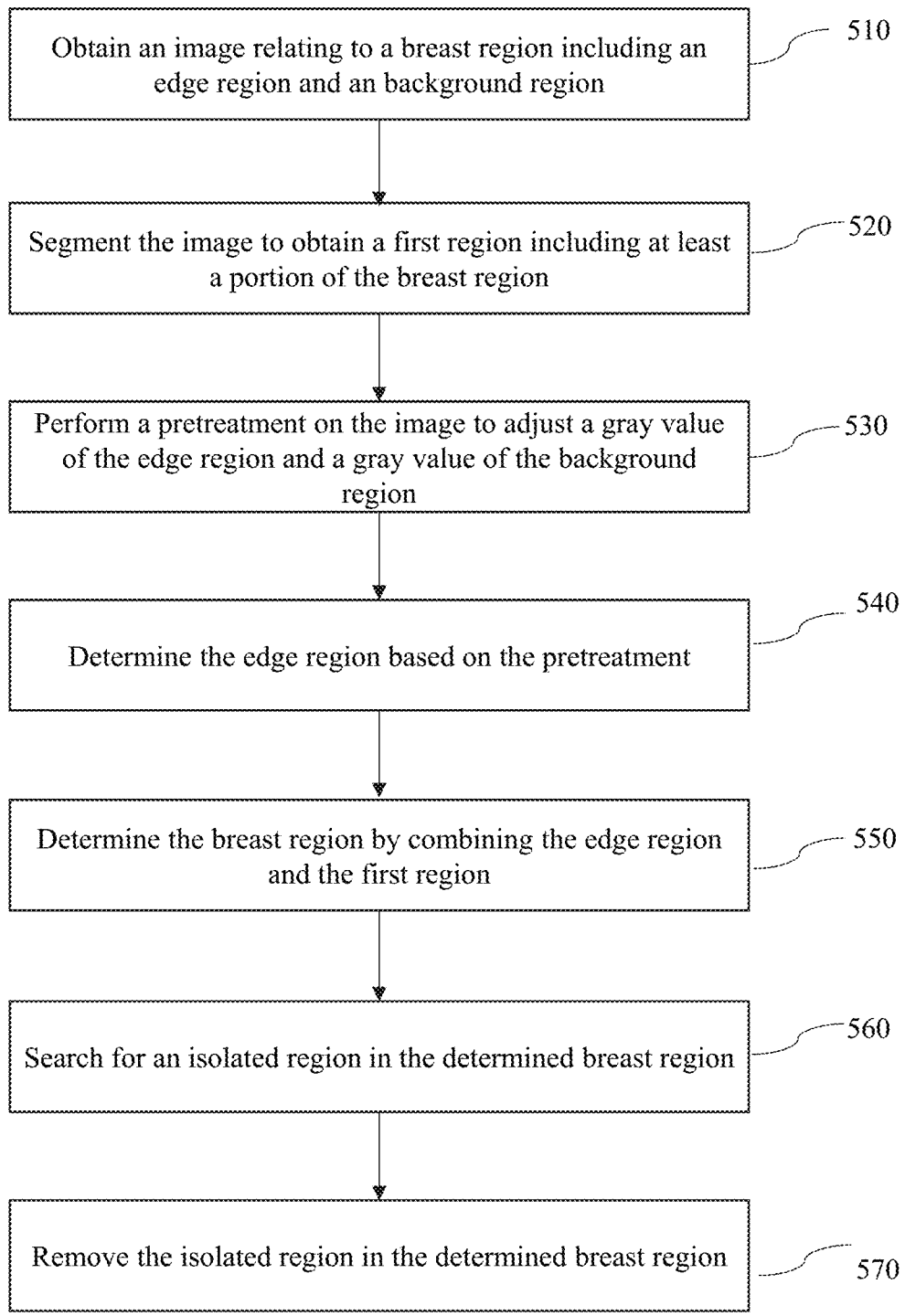
FIG. 5 is a flowchart illustrating a process 500 for identifying an edge of a breast region according to some embodiments of the present disclosure.

FIG. 5 is a flowchart illustrating a process 500 for identifying an edge of a breast region according to some embodiments of the present disclosure. In 510, an image relating to a breast region may be obtained. In some embodiments, the image may include a background region.

In 520, a first region may be segmented from the image. The first region may include at least a portion of the breast region. In some embodiments, the first region may be segmented based on a threshold segmentation algorithm as described elsewhere in the disclosure. For example, a gray value threshold may be determined; a pixel in the image whose a gray value is below the gray value threshold may be designated as belonging to the first region; a pixel in the image whose gray value exceeds or is equal to the gray value threshold may be designated as belonging to the background region.

Merely by way of example, the first region may be determined based on the Otsu's algorithm. For those skilled in the art, a gray value histogram may provide a distribution map of the gray values of the pixels. For instance, the gray value histogram of the image including a breast region may include two peaks corresponding to two classes of pixels in the image. According to the Otsu's algorithm, an image may contain two classes of pixels including foreground pixels and background pixels. The foreground pixels and background pixels may correspond to the breast region and the background region, respectively. Thus, the Otsu's algorithm may be used to identify the breast region in the image.

As another example, the first region may be determined via the Watershed Algorithm, which may include an iterative process of labeling. The gradient magnitude of gray value of pixels in the image may include a plurality of local minimum gradient magnitude each of which may be given a different label. The pixels surrounding the pixels with local minimum gradient magnitude may form a plurality of minimum regions. The plurality of minimum regions may be connected to form the first region and one or more other regions (e.g., a background region).

In some embodiments, the image may be pretreated before the first region is segmented such that the first region may be distinguishable from one or more other regions. Exemplary pretreatment may include image enhancing, image denoising, image smoothing, or the like, or a combination thereof.

In 530, a pretreatment may be performed on the image to adjust an average gray value in different regions in the image. The average gray value of pixels may be a ratio between a sum of the gray values of all pixels in a region and the number of pixels in that region. The first region may include a first plurality of pixels corresponding to a first average gray value. The edge region may include a second plurality of pixels corresponding to a second average gray value, and the background region may include a third plurality of pixels corresponding to a third average gray value. The gray values corresponding to the second plurality of pixels in the edge region may change discontinuously. In some embodiments, before the pretreatment, the first average gray value may be smaller than the second average gray value in the image. Similarly, the third average gray value may be greater than the second average gray value in the image. The second average gray value may be close to the third average gray value, which may make it difficult to distinguish the edge region and the background region.

The pretreatment on the image may adjust the second average gray value corresponding to the second plurality of pixels and the third average gray value corresponding to the third plurality of pixels, such that the edge region may be distinguishable from the background region via a certain algorithm. The adjustment may further adjust the gray values of the first plurality of pixels such that the first average gray value is smaller than the second average gray value, and that the first average gray value is greater than the third average gray value. The pretreatment may include a first pretreatment on the image to obtain a first image, and/or a second pretreatment on the first image to obtain a second image.

In some embodiments, the first pretreatment may include a gradient transform or a differential operation on the image to obtain the first image. In some embodiments, the second pretreatment on the first image may include: obtaining a third image via a negative film operation on the image, and multiplying the first image and the third image to obtain the second image. In some embodiments, the third image may be normalized before it is multiplied with the first image.

In some embodiments, the first pretreatment may include a denoising operation on the image to obtain the first image. In some embodiments, the second pretreatment may include a gradient transform or a differential operation on the first image to obtain the second image. In some embodiments, the first image may be obtained by performing a logarithm transform on the image before the denoising operation. In some embodiments, the logarithm transform may enhance the first average gray value while weaken the third average gray value such that the first average gray value may be greater than the third average gray value in the first image.

In some embodiments, the gradient transform may be performed by applying a Roberts operator, a Prewitt operator, a Sobel operator, a Kirsch operator, a Compass operator, a Marr-Hildreth operator, a Canny operator, a Laplacian operator, or the like, or a combination thereof. In some embodiments, the denoising operation may be performed by using a spatial-domain filter, a transform-domain filter, a morphological noise filter, or the like, or a combination thereof. The spatial-domain filter may include a field average filter, a median filter, a low-pass filter, or the like, or a combination thereof. The transform-domain filter may perform a Fourier transform, a Walsh-Hadamard transform, a cosine transform, a K-L transform, a wavelet transform, or the like, or a combination thereof. The morphological noise filter may perform an expansion operation, a corrosion operation, an open operation, a closed operation, a hit and miss transform, or the like, or a combination thereof. In some embodiments, the denoising operation may be performed by applying a partial differential equation or a variational technique. The partial differential equation may include a Perona equation, a Malik equation, or the like, or a combination thereof. The variational technique may include applying a total variational model.

In 540, the edge region may be determined based on the pretreatment. As described above, the second average gray value may be greater than the third average gray value, and the third average gray value may be smaller than the first average gray value after the pretreatment. The edge region and the background region may be distinguishable based on, for example, a threshold segmentation algorithm as described elsewhere in the disclosure. Merely by way of example, a gray value threshold may be calculated based on the threshold segmentation algorithm. A pixel in the image having a gray value greater than the gray value threshold may be designated as belonging to the edge region, while a pixel in the image having a gray value smaller than the gray value threshold may be designated as belonging to the background region.

In 550, the breast region may be determined by combining the edge region and the first region. In some embodiments, the determined breast region may be a binary image. For example, the gray value of pixels in the binary image may be set as "0" or "1." For illustrative purposes, the binary image may be formed as follows. In a first image, the gray value of pixels in the segmented first region obtained in 520 may be set to be "1," and the gray value of pixels in one or more other regions except for the first region may be set to be "0." In a second image, the gray values of pixels in the determined edge region obtained in 540 may be set to be "1," and the gray values of pixels in one or more other regions except for the edge region may be set to be "0."

The breast region may be obtained by adding the first image to the second image. As used herein, adding two images may refer to adding the gray values of two corresponding pixels in the determined first region and the determined edge region to form a combined image. As used herein, two corresponding pixels in two images may refer to two pixels in the two images that correspond to a same physical location or spot of a subject represented the images. In some embodiments, the second plurality of pixels in the determined edge region may include at least one of the first plurality of pixels in the determined first region. If a gray value of a pixel in the combined image after the addition is "2," the gray value of the pixel may be updated to "1," and the pixel may be designated as belonging to the breast region. If a gray value of a pixel in the combined image after the addition is "1," the pixel may be designated as belonging to the breast region. If a gray value of a pixel in the combined image after the addition is "0," the pixel may be designated as belonging to the background region. The breast region may be a set of pixels each with gray value "1."

In 560, an isolated region in the determined breast region may be searched for. In some embodiments, the isolated region may include at least one pixel. In some embodiments, the gray values of pixels in the isolated region may be different from the gray values of the pixels surrounding the isolated region. For example, the isolated region may include a set of pixels with a gray value of "0" in the determined breast region, while the gray values of pixels surrounding the isolated region may be "1."

In 570, the isolated region in the determined breast region may be removed. For example, if the isolated region lies in the breast region the gray values of whose pixels are "0," the gray value of pixels in the isolated region may be changed to "1." If the isolated region lies in the background region the gray values of whose pixels are "1," the gray values of pixels in the isolated region may be changed to "0."

It should be noted that the flowchart depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the 520 may be performed simultaneously with 530 and 540. In some embodiments, the 560 and 570 for determining the isolated region may be unnecessary.

Figure 6:
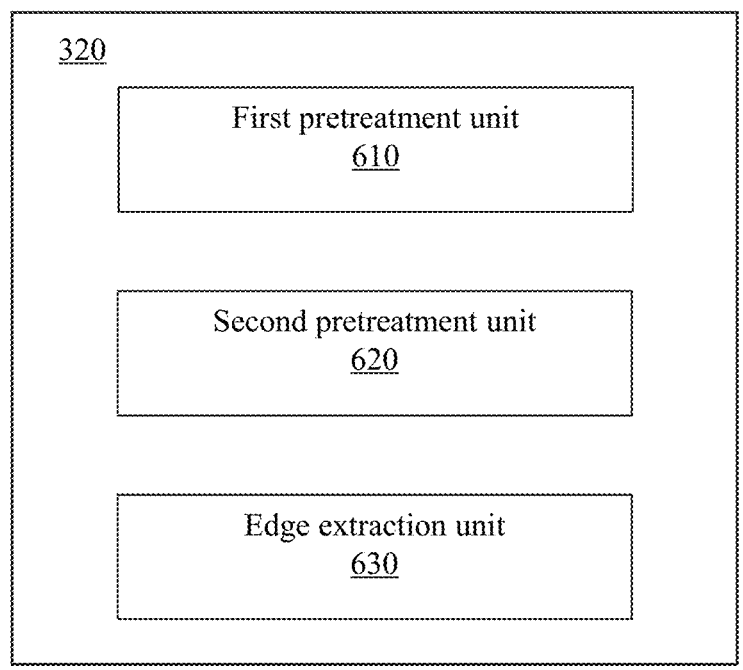
FIG. 6 is an exemplary block diagram of the edge identification sub-module 320 according to some embodiments of the present disclosure.

FIG. 6 is an exemplary block diagram of the edge identification sub-module 320 according to some embodiments of the present disclosure. As shown in FIG. 6, the edge identification sub-module 320 may include a first pretreatment unit 610, a second pretreatment 620, and an edge extraction unit 630.

The first pretreatment unit 610 may perform a first pretreatment on an image to obtain a first image. The image may be obtained from the storage module 220, or may be obtained from an external device, e.g., the imaging device 110 or the database 120 via the input module 230. The first pretreatment may be performed to adjust the gray values of pixels in the image as illustrated in 530. The first pretreatment may include a gradient transform, a logarithmic transformation, a Gamma transformation, a gray stretch operation, a gray slicing operation, a denoising operation, or the like, or a combination thereof.

In some embodiments, the gradient transform may be performed by applying a Roberts operator, a Prewitt operator, a Sobel operator, a Kirsch operator, a Compass operator, a Marr-Hildreth operator, a Canny operator, a Laplacian operator, or the like, or a combination thereof.

The denoising operation may include applying a spatial-domain filter, a transform-domain filter, a morphological noise filter, or the like, or a combination thereof. The spatial-domain filter may include a field average filter, a median filter, a Gaussian filter, or the like, or a combination thereof. The transform-domain filter may perform a Fourier transform, a Walsh-Hadamard transform, a cosine transform, a K-L transform, a wavelet transform, or the like, or a combination thereof. The morphological noise filter may perform an expansion operation, a corrosion operation, an open operation, a closed operation, a hit and miss transform, or the like, or a combination thereof. In some embodiments, the denoising operation may be performed by applying a partial differential equation or a variational technique. The partial differential equation may include a Perona equation, a Malik equation, or the like, or a combination thereof. The variational technique may include applying a total variational model.

The second pretreatment unit 620 may perform a second pretreatment on the first image obtained in the first pretreatment unit 610. The second pretreatment may be performed to adjust the gray values of pixels in the image as illustrated in 530. In some embodiments, the second pretreatment may be performed to enhance the gray values of the pixels in the first region and decrease the gray values of the pixels in the background region as illustrated in 530.

In some embodiments, the second pretreatment may include a gradient transform, a negative film, a normalization operation, a Gamma transformation, a gray stretch operation, a gray slicing operation, or the like, or a combination thereof.

In some embodiments, the second pretreatment may include multiplying the image obtained after the first pretreatment with an image obtained after a negative film operation on the image.

The edge extraction unit 630 may determine an edge region based on the pretreatment on the image as illustrated in 540. The edge region may be determined from the pretreated image as illustrated in 540 via a threshold segmentation algorithm as described elsewhere in the disclosure including, for example, the Otsu's algorithm, the iterative algorithm, etc.

It should be noted that the block diagram depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the first pretreatment unit 610 may include a denoising sub-unit or a gradient transform sub-unit. In some embodiments, the second pretreatment 620 unit may include a gradient transform sub-unit. In some embodiments, the first pretreatment unit 610 and the second pretreatment unit 620 may be integrated into one unit.

Figure 7:
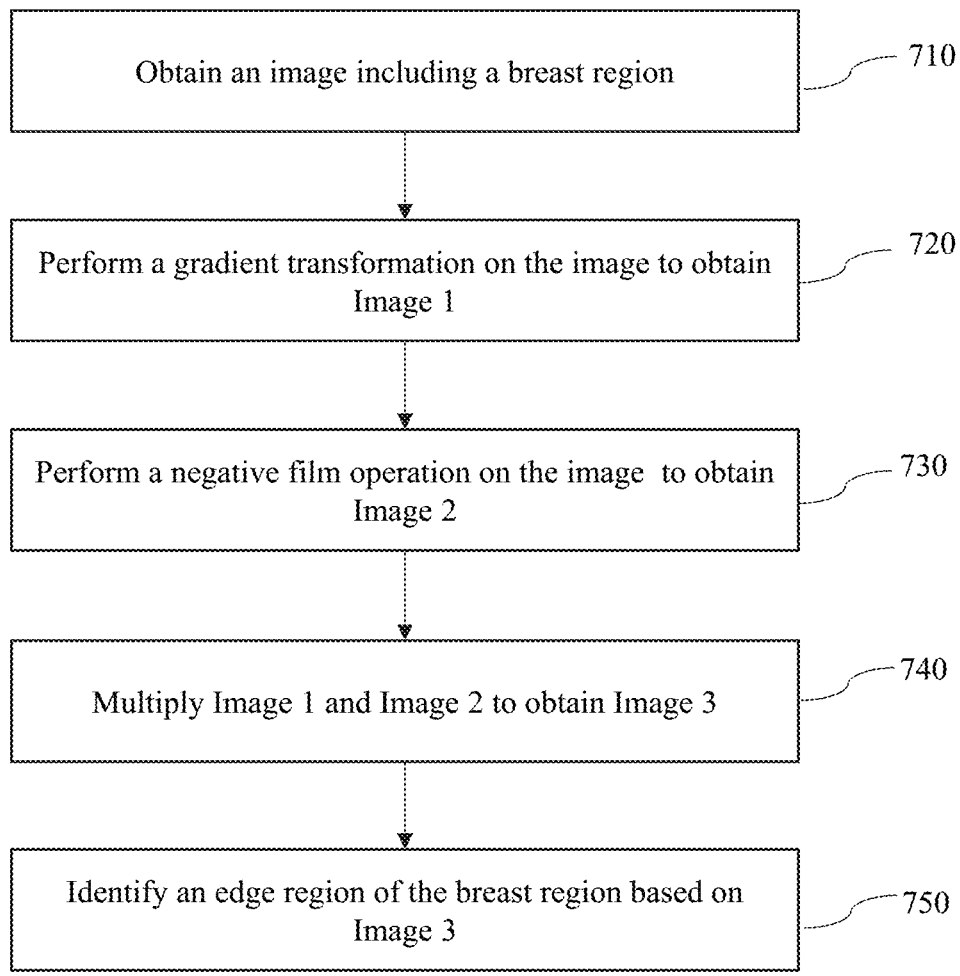
FIG. 7 is an exemplary flowchart illustrating a process 700 for determining the edge region according to some embodiments of the present disclosure.
Figure 13:
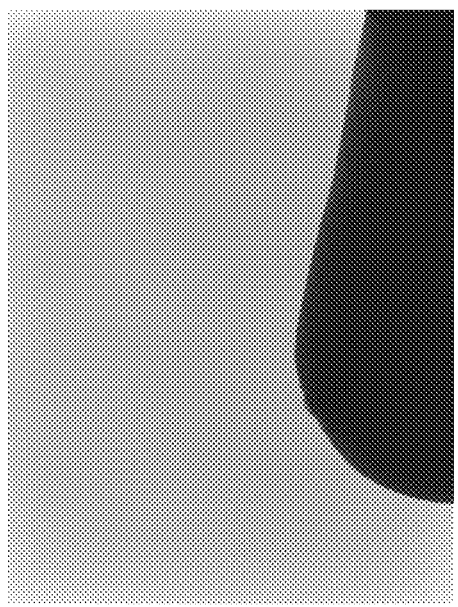
FIG. 13 is an exemplary image including a breast region according to some present disclosure.

FIG. 7 is an exemplary flowchart illustrating a process 700 for determining the edge region according to some embodiments of the present disclosure. In 710, an image may be obtained. In some embodiments, the image may include a breast region. In some embodiments, the image may be a medical image as described elsewhere in the disclosure. As shown in FIG. 13, a medical image may be generated via an FFDM system.

In 720, Image 1 may be obtained by performing a gradient transform on the image obtained in 710. The gradient transform may be similar to the first pretreatment as described in 530 in FIG. 5. In some embodiments, the gradient transform may be performed to enhance the gray values of pixels in the edge region of the breast region such that the average gray value of the pixels in the edge region exceed the average gray value of the pixels in the background region. In some embodiments, the gradient transform may be performed based on a gradient operator including a Robert operator, a Sobel operator, a Prewitt operator, a Log operator, a Canny operator, or the like, or a combination thereof.

In 730, Image 2 may be obtained by performing a negative film operation on the image obtained in 710. A highest gray value of the pixels in the image may be identified. Image 2 may be obtained by subtracting the gray value of each pixel in the image from the highest gray value. The average gray value of pixels in the background region (e.g., the third average gray value illustrated in 530) may be smaller than the average gray value of pixels in the edge region (e.g., the second average gray value illustrated in 530) or the average gray value of the pixels in the first region (e.g., the first average gray value illustrated in 530).

In some embodiments, Image 2 may be obtained by performing a normalization operation after the negative film operation. The normalization operation may be a Min-Max scaling, a Z-score standardization, or the like, or a combination thereof. In some embodiments, the normalization may be performed on pixels values (e.g., gray values) of pixels in Image 2. For example, the normalization may include dividing each pixel value of Image 2 by a scale. The scale may be set by default, by a user, or by a device.

In 740, Image 3 may be obtained by multiplying Image 1 and Image 2. In image 3, the average gray value of the pixels in the first region (e.g., the first average gray value) may be smaller than the average gray value of the pixels in the edge region (e.g., the second average gray value), while may be greater than the gray average value of the pixels in the background region in Image 3 (e.g., the third average gray value). The operations in 730 and 740 may be similar or correspond to the second pretreatment as described in 530 in FIG. 5.

In 750, the edge region may be identified based on Image 3 via an iterative algorithm. The iterative algorithm may include one or more of the following operations. (a) The highest gray value and the lowest gray value of the pixels in Image 3 may be identified. (b) A half of the sum of the highest gray value and the smallest gray value may be set as a gray value threshold $T_{i-1}$ for the iteration. For the first iteration, the initial gray value threshold may be referred to as $T_0$. (c) Image 3 may be divided into a first portion and a second portion based on the gray threshold $T_{i-1}$. A pixel whose gray value is greater than the initial gray threshold $T_{i-1}$ may be assigned to the first portion. A pixel whose gray value is lower than the initial gray threshold T may be assigned to the second portion. (d) An average gray value of the pixels in the first portion and an average gray value of the pixels in the second portion may be determined, respectively. An average gray value of pixels may be a ratio between a sum of the gray values of all pixels in each portion and the number of pixels in that portion. (e) A half of the sum of the average gray value of the pixels in the first portion and the average gray value of pixels in the second portion may be designated as a new gray threshold $T_i$. (f) A determination may be made as to whether the absolute value of $(T_i-T_{i-1})$ is greater than a predetermined value (e.g., "1", or any other suitable value). If the absolute value of $(T_i-T_{i-1})$ is equal to or lower than 1, the $T_1$ may be regarded as the optimal gray threshold T. If the absolute value of $(T_1-T_0)$ is greater than 1, the initial gray threshold $T_0$ may be updated to assume the value of $T_1$, and Image 3 may be divided to two new portions, a new first portion and a new second portion, based on $T_i$; repeating (d)-(f) until the absolute value of $(T_i-T_{i-1})$ is less than 1 when $T_i$ may be determined to be the optimal gray threshold T. (g) Image 3 may be segmented based on the optimal gray threshold T. The edge region may include a set of pixels whose gray values exceed the optimal gray threshold T.

It should be noted that the operations depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the distribution of the gray values of pixels in Image 3 may be obtained based on other operations such that the average gray value of the pixels in the first region is greater than the average gray value of the pixels in the background region and that the average gray value of the pixels in the first region is smaller than the average gray value of the pixels in the edge region.

Figure 8:
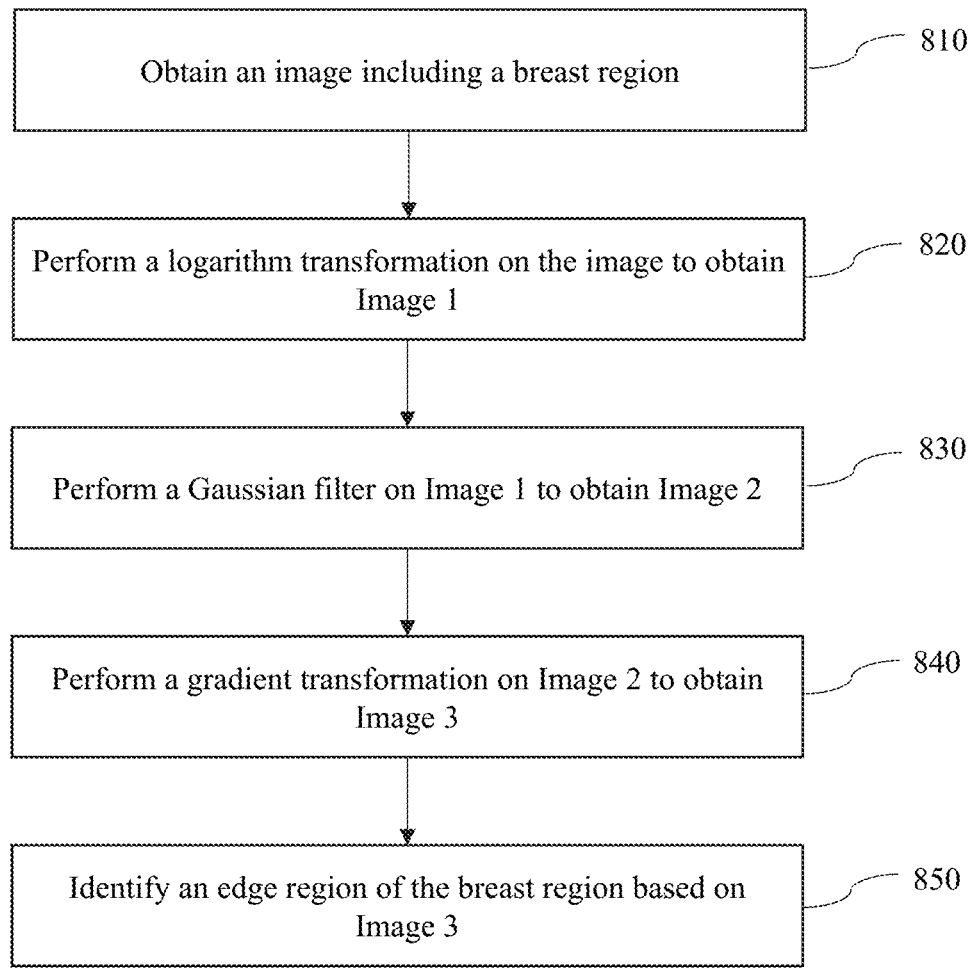
FIG. 8 is an exemplary flowchart illustrating a process 800 for determining the edge region according to some embodiments of the present disclosure.

FIG. 8 is an exemplary flowchart illustrating a process 800 for determining the edge region according to some embodiments of the present disclosure. In 810, an image may be obtained. In some embodiments, the image may include a breast region. In some embodiments, the image may be a medical image as described elsewhere in the disclosure.

In 820, Image 1 may be obtained by performing a logarithm transformation on the image obtained in 810. The logarithm transformation may be performed to enhance the gray values of the pixels in the edge region of the breast region and weaken the gray values of the pixels in the background region such that the average gray value of the pixels in the edge region are greater than the average gray value of the pixels in the background region.

In 830, Image 2 may be obtained by performing a denoising operation on Image 1 obtained in 820. In some embodiments, the denoising operation may be based on a Gaussian filter. The Gaussian filter may reduce the noise in the gray values of the pixels in the edge region and in the gray values of the pixels in the background region. In some embodiments, the Gaussian filter may include a Fourier transform, a discretization window discretization, or the like, or a combination thereof. The operations in 820 and 830 may be similar or correspond to the first pretreatment as described in 530 in FIG. 5.

In 840, Image 3 may be obtained by performing a gradient transform on Image 2 obtained in 830. The operation in 840 may be similar or correspond to the second pretreatment as described in 530 in FIG. 5. In some embodiments, the gradient transform may be performed to enhance the gray values of the pixels in the edge region. In some embodiments, the gradient transform may be performed by a gradient operator including a Robert operator, a Sobel operator, a Prewitt operator, a Log operator, a Canny operator, or the like, or a combination thereof. In Image 3, the average gray values of the pixels in the first region (e.g., the first average gray value) may be smaller than the average gray value of the pixels in the edge region (e.g., the second average gray value), while the average gray value of the pixels in the first region (e.g., the first average gray value) may be greater than the average gray value of the pixels in the background region (e.g., the third average gray value).

In 850, an edge region may be identified based on Image 3 obtained in 840 via the Otsu's algorithm. The Otsu's algorithm may include one or more of the following operations. (a) A gray value histogram of pixels in Image 3 may be calculated. (b) A gray threshold Ti may be set from the gray values in the gray value histogram of pixels in Image 3. (c) Image 3 may be divided into a target portion and a background portion based on the gray threshold Ti. (d) A inter-class variance between the gray values of pixels in the target portion and the gray values of pixels in the background portion may be determined based on the gray value histogram of pixels and the gray threshold Ti. (e) Steps (b)-(d) may be performed repeatedly until determining an optimal gray threshold T when the inter-class variance between the target portion and the background portion maximum. (f) Image 3 may be divided based on the optimal gray threshold T. The edge region may be determined by a set of pixels whose gray values exceed the optimal gray threshold T.

It should be noted that the operations depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, a distribution of the gray values of the pixels in Image 3 may be obtained based on other operations such that the average gray value of the pixels in the first region is greater than the average gray value of the pixels in the background region and that the average gray value of the pixels in the first region is smaller than the average gray value of the pixels in the edge region. In some embodiments, 820 may be unnecessary.

Figure 9:
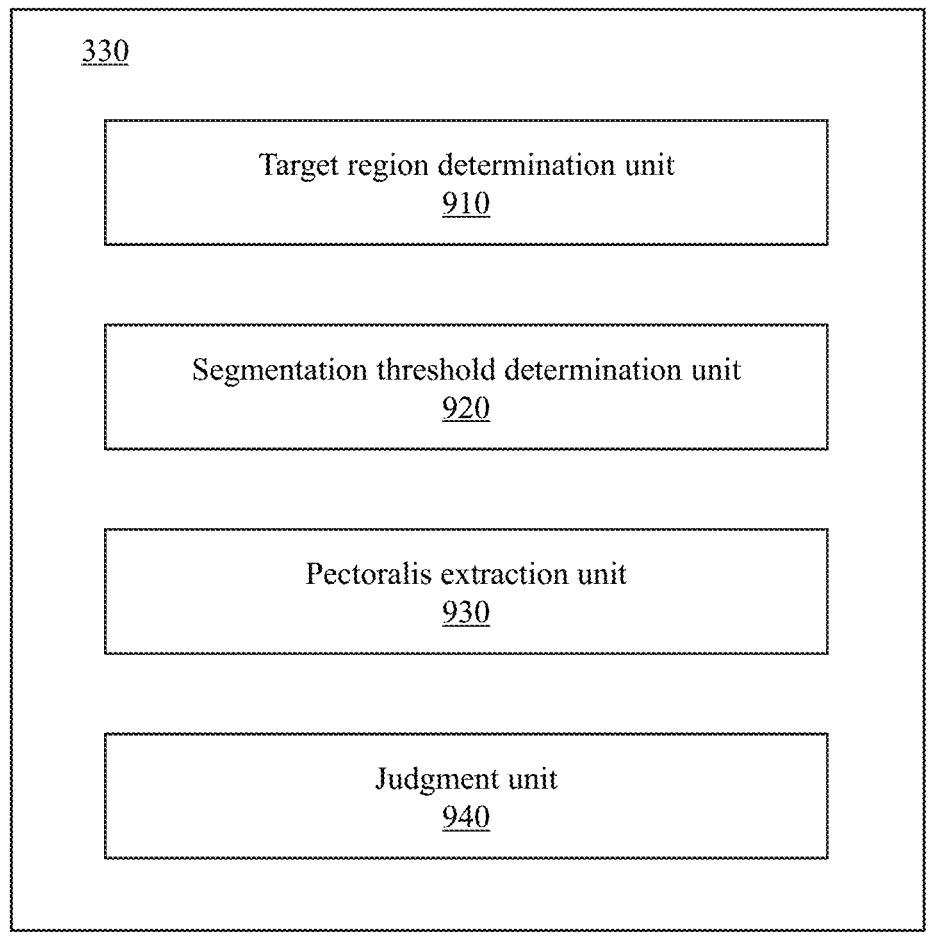
FIG. 9 illustrates an exemplary block diagram of the pectoralis identification sub-module 330 according to some embodiments of the present disclosure.

FIG. 9 illustrates an exemplary block diagram of the pectoralis identification sub-module 330 according to some embodiments of the present disclosure. The pectoralis identification sub-module 330 may include a target region determination unit 910, a segmentation threshold determination unit 920, a pectoralis extraction unit 930, and a judgment unit 940.

The target region determination unit 910 may determine a target region in a breast region in an image. The image may be a medical image as described elsewhere in the disclosure. In some embodiments, the target region may include a pectoralis sub-region. The target region determination unit 910 may determinate the pectoralis sub-region by determining one or more points relating to the pectoralis sub-region in the image. In some embodiments, the points may be determined based on one or more characteristics of the pectoralis sub-region. Exemplary characteristics may include the shape of the pectoralis sub-region, the size of the pectoralis sub-region, the position of the pectoralis sub-region, the structure of the pectoralis sub-region, or the like, or a combination thereof.

The segmentation threshold determination unit 920 may determine a gray value threshold in the target region. In some embodiments, the gray value threshold may be determined based on one or more characteristics of a gray value histogram of the target region as described elsewhere in the disclosure. The target region may be segmented into one or more sub-regions of interest (e.g., a pectoralis sub-region) based on the gray value threshold. In some embodiments, the segmentation threshold determination unit 920 may include a calculation sub-unit, a normalization sub-unit and a search sub-unit (not shown in the figure). The calculation sub-unit may generate a first gray value histogram of the target region based on the gray values of the pixels in the target region. The first gray value histogram including a plurality of gray values in the target region and the number of pixels in the target region having a same gray value of the plurality of gray values. The normalization sub-unit may perform a normalization operation on the first gray value histogram to generate a second gray value histogram of the target region. The second gray value histogram including a plurality of normalized gray values in the target region and the number of pixels in the target region having a same normalized gray value of the plurality of normalized gray values. In some embodiments, the segmentation threshold determination unit 920 may perform a pretreatment on the first gray value histogram to bring about an adjustment to the target region. The adjustment may include an increase or decrease the area of the target region, a gray value range in the gray value histogram of the target region, etc.

In some embodiments, the gray value threshold may be determined based on a threshold segmentation algorithm as described elsewhere in the disclosure including, for example, the Otsu's algorithm, the iterative algorithm, etc.

The pectoralis extraction unit 930 may determine the pectoralis sub-region based on a gray value threshold obtained from the segmentation threshold determination unit 920. For illustrative purposes, a pixel in the target region whose gray value is smaller than the gray value threshold may be assigned to the pectoralis sub-region.

The judgment unit 940 may determine whether the pectoralis sub-region is correctly determined. In some embodiments, the judgment unit 940 may determine whether a boundary of the pectoralis sub-region intersects with a boundary of the target region. If the two boundaries intersect, the determination of the pectoralis sub-region may be deemed improper; otherwise, the determination of the pectoralis sub-region may be deemed proper. In some embodiments, the judgment unit 940 may include an update sub-unit. The update sub-unit may update the target region with respect to the intersection between the boundary of the pectoralis sub-region and the boundary of the target region.

It should be noted that the block diagram depicted above is provided for the purposes of illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the segmentation threshold determination unit 910 and the segmentation threshold determination unit 920 may be integrated into one unit. In some embodiments, the pectoralis extraction unit 930 and the segmentation threshold determination unit 920 may be integrated into one unit. In some embodiments, the judgment unit 940 and the pectoralis extraction unit 930 may be integrated into one unit. In some embodiments, the pectoralis identification sub-module 330 may include a controller unit. The controller unit may control or coordinate the units in the pectoralis identification sub-module 330 to determine the pectoralis sub-region.

Figure 10:
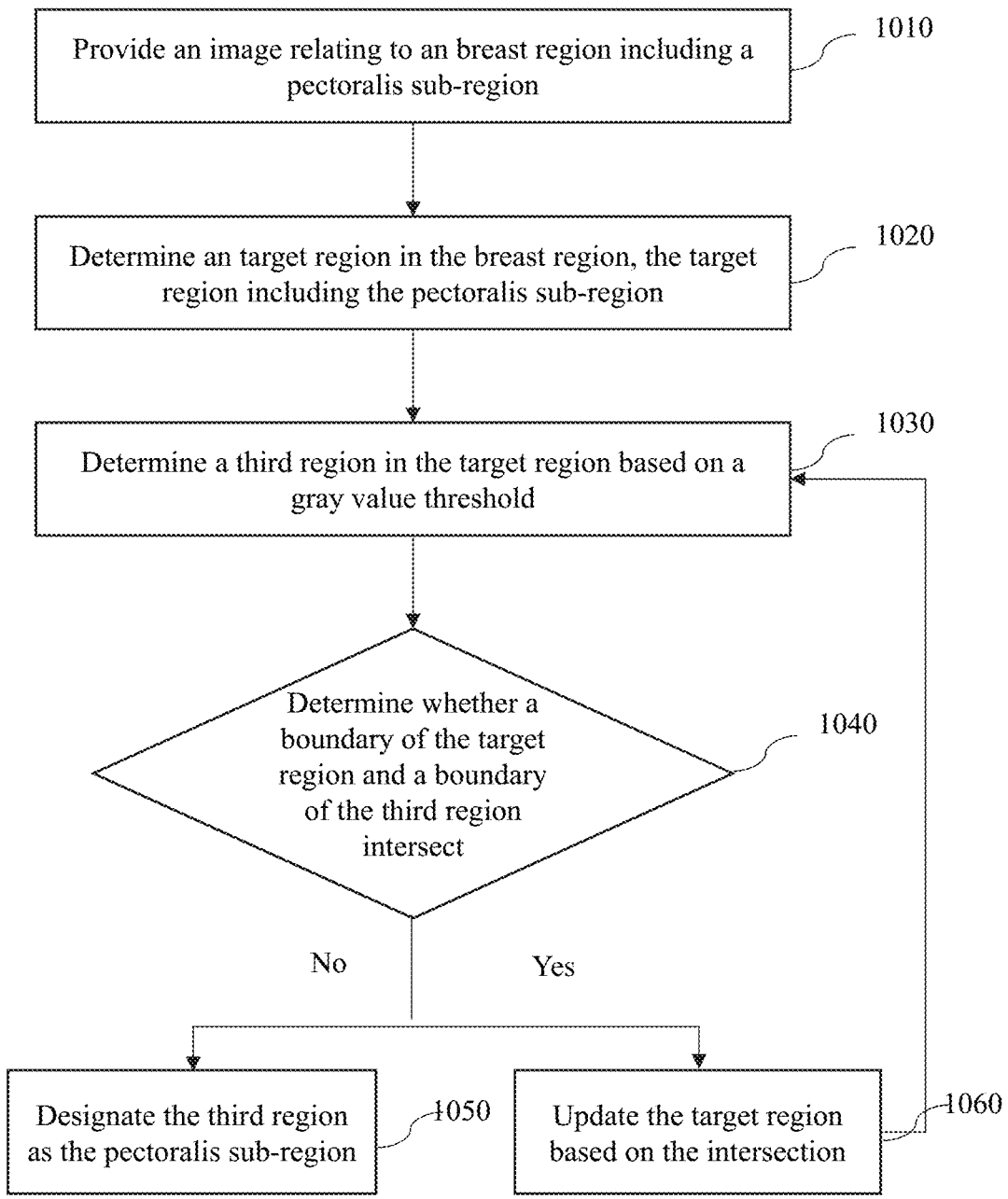
FIG. 10 is a flowchart illustrating a process 1000 for determining a pectoralis sub-region in a breast region according to some embodiments of the present disclosure.

FIG. 10 is a flowchart illustrating a process 1000 for determining a pectoralis sub-region in a breast region according to some embodiments of the present disclosure. The process may be performed by the pectoralis identification sub-module 330.

In 1010, an image relating to a breast region may be provided. In some embodiments, the image may be a medical image as described elsewhere in the disclosure. In some embodiments, the breast region in the image may be determined based on the process as described in FIG. 5. In some embodiments, the breast region may be determined based on a segmentation technique as described elsewhere in the disclosure.

In step 1020, a target region may be determined in the breast region. In some embodiments, the target region may include at least a pectoralis sub-region. In some embodiments, the target region may be determined based on a characteristic of the pectoralis sub-region as described elsewhere in the disclosure. Exemplary characteristics of the pectoralis sub-region may include the shape of the pectoralis sub-region, the size of the pectoralis sub-region, the position of the pectoralis sub-region, the structure of the pectoralis sub-region, or the like, or a combination thereof. For example, the pectoralis sub-region in the image relating to the breast region may be approximately a triangle. Accordingly, the target region may be set as a right triangular. Furthermore, the target region may be determined to be at the edge of the breast region on the ground that the position of the pectoralis sub-region may lie at the edge of the breast region in the image. In some embodiments, the target region may be determined based on a characteristics of the breast region including the breast shape, the breast size, the breast structure, etc. As used herein, the breast structure may include the thickness of the fat tissue in the breast, the ratio of the fat tissue to other tissues in the breast, the connective tissue in the breast, etc.

In some embodiments, before the target region is determined, a treatment may be performed on the image provided in 1010. The treatment may include a denoising operation, a background segmentation, an image rollover, or the like, or a combination thereof. In some embodiments, the image rollover may be performed to change the position of the pectoralis sub-region to, for example, a certain area (e.g., the upper-left of the image).

In 1030, a third region may be determined in the target region based on a gray value threshold. In some embodiments, the third region may be the pectoralis sub-region described elsewhere in the disclosure. In some embodiments, the third region may include a portion of the pectoralis sub-region that may be further segmented.

In some embodiments, the gray value threshold may be determined based on a characteristic of a gray value histogram of the target region. Exemplary characteristics of a gray value histogram may include a shape of the gray value histogram, a changing rate of pixels number in the gray value histogram, a peak gray value in the gray value histogram, a first-order derivative of the gray value histogram, a second-order derivative of the gray value histogram, or the like, or a combination thereof. Merely by way of example, a changing rate of the pixel numbers corresponding to gray values in the pectoralis sub-region or one or more other sub-regions in the target region is smaller than a changing rate of the pixel numbers corresponding to gray values in a transition region between the pectoralis sub-region and the one or more other sub-regions. Therefore, the gray value threshold may be determined based on the greatest change rate of the pixel numbers in the gray value histogram of the target region. In some embodiments, the greatest change rate of the pixel numbers may be determined based on the first-order derivative of the pixel numbers in the gray value histogram of the target region. In some embodiments, the greatest change rate may be determined based on the second-order derivative of the pixel numbers in the gray value histogram of the target region.

In some embodiments, the gray value threshold may be determined by a threshold segmentation algorithm as described elsewhere in the disclosure. For example, the gray value threshold may be determined based on the Otsu's algorithm.

In some embodiments, when the gray value threshold is determined, the gray value of a pixel in the target region may be compared with the gray value threshold. If a pixel whose gray value is smaller than the gray value threshold may be designated as belonging to the third region.

In 1040, a determination may be made as to whether a boundary of the target region intersects with a boundary of the third region. In some embodiments, the boundary of the third region may be determined by a curve fitting a plurality of pixels on the boundary of the third region, including multiple terms fitting such as, quadratic term fitting, Gaussian function fitting, or the like, or a combination thereof. In some embodiments, the boundary of the target region may be the hypotenuse of a right triangle, and the boundary of the third region may be a fitting curve as described above.

If the boundary of the target region does not intersect with the boundary of the third region, the process 1000 may proceed to 1050, where the third region may be designated as the pectoralis sub-region.

If the boundary of the target region intersects with the boundary of the third region, the process 1000 may proceed to 1060, where the target region may be updated based on the intersection of the boundary of the target region and the boundary of the third region. Then, the process 1000 may go back to step 1030 to determine a new third region, and repeat the process from 1030 to 1060 until the boundary of the updated target region does not intersect with the boundary of the third region.

It should be noted that the flowchart depicted above is provided for the purposes of illustration, and not intended to limit the scope of the present disclosure. For persons having ordinary skills in the art, various variations and modification may be conducted under the teaching of the present disclosure. However, those variations and modifications may not depart the scope of the present disclosure.

Figure 11:
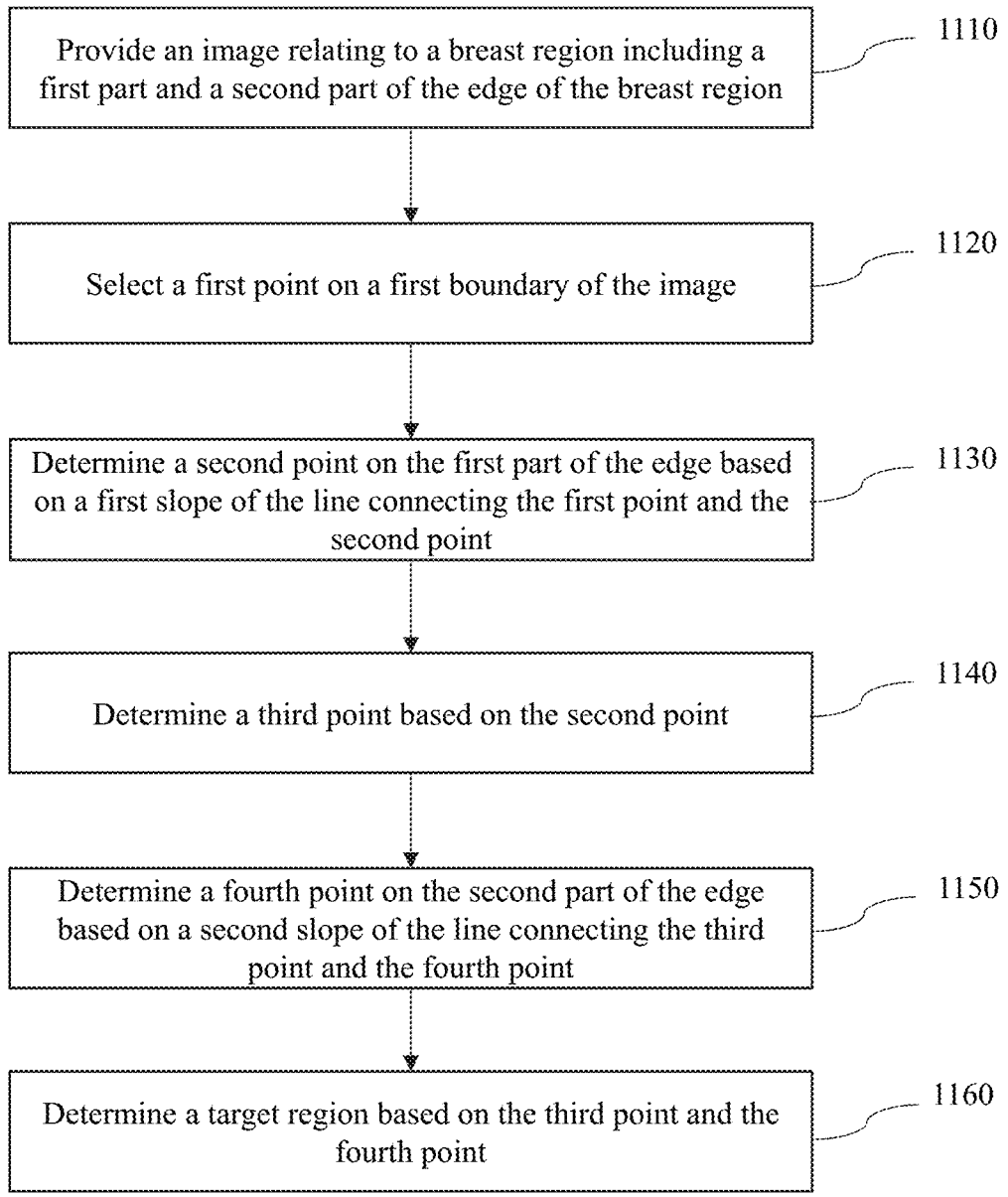
FIG. 11 is a flowchart illustrating a process 1100 for determining a target region according to some embodiments of the present disclosure.

FIG. 11 is a flowchart illustrating a process 1100 for determining a target region according to some embodiments of the present disclosure. The process may be performed by the target region determination unit 910.

Figure 15:
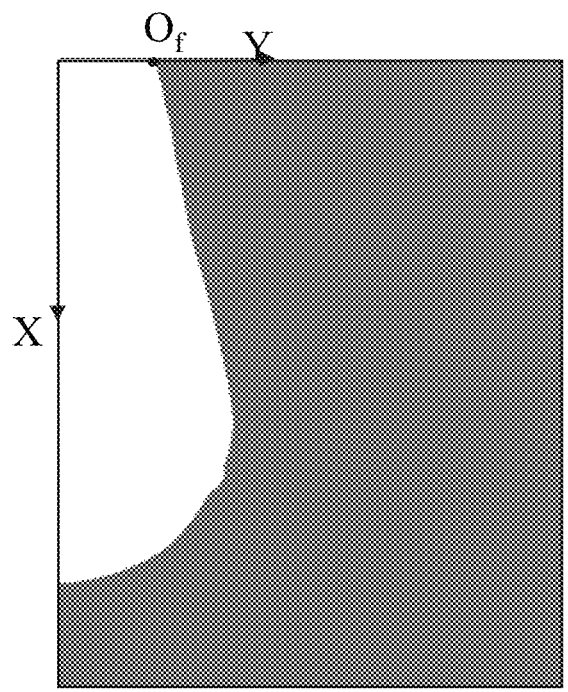
FIGS. 15-19 are diagrams illustrating a process for a target region determining according to some embodiments of the present disclosure.

In 1110, an image relating to a breast region may be provided. In some embodiments, the image may be a medical image as described elsewhere in the disclosure. In some embodiments, the breast region may be determined based on a segmentation technique as illustrated in FIG. 5. The image may include an edge of the breast region, which further may include a first part and a second part. The image may include a first boundary (e.g., a horizontal boundary) and a second boundary (e.g., a vertical boundary), as shown in FIG. 15.

Figure 16:
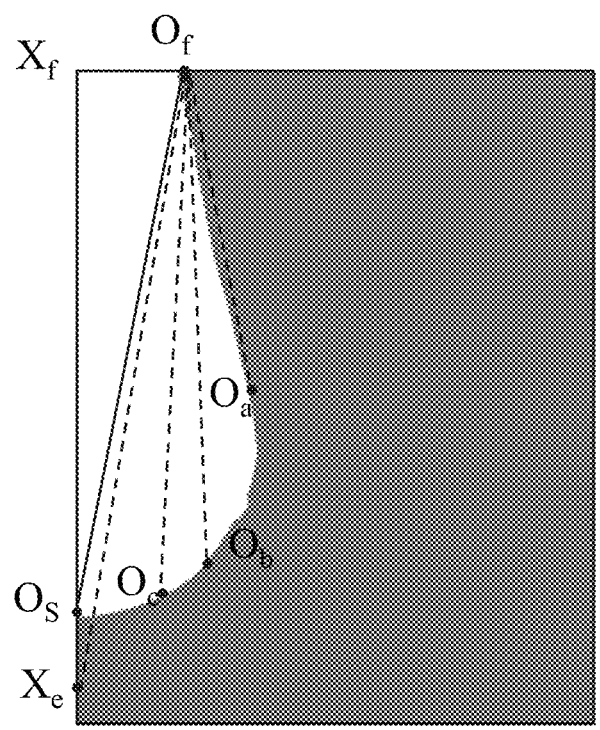

In 1120, a first point may be selected on the first boundary of the image. In some embodiments, the first point may be selected based on a predetermined parameter in the system 100. In some embodiments, the first point may be selected based on a machine learning process by studying abundant images including breast regions. It shall be noted that the first point may be selected at different locations on the first boundary. For better understanding of the disclosure, FIG. 16 is taken as an example to illustrate the selection of different points, while the description is merely provided for the purposes of illustration, and not intended to limit the scope of the present disclosure. The first point may be the intersection point between the horizontal boundary of the image and the edge of the breast region in the image, i.e., the point $Q_f$ in FIG. 16.

In 1130, a second point may be determined on a first part of the edge of the breast region based on a first slope of the line connecting the first point and the second point. In some embodiments, the length of the first part of the edge of the breast region may be a distance from an end point on the edge of the breast region (e.g., the point $X_e$ in FIG. 16) to another point on the edge of the breast region (e.g., the point $O_a$ in FIG. 16). In some embodiments, the length may be in a range from 0.5 $L_b$ to 0.7 $L_b$, where $L_b$ may be a distance in the vertical direction from a start point (e.g., the point $O_f$ in FIG. 16) and an end point (e.g., the point $X_e$ in FIG. 16) on the edge of the breast region (e.g., the distance between the point $X_f$ and the point $X_e$ in FIG. 16). The slope of the line connecting the first point (e.g., the point $Q_f$ in FIG. 16) and each point on the first part of the edge (e.g., the point $O_a$, the point $O_b$, the point $O_e$ in FIG. 16) may be calculated. In some embodiments, the point corresponding to a minimum slope of the lines may be selected as the second point (e.g., the point $O_s$ in FIG. 16).

In 1140, a third point may be determined based on the second point. A distance from the third point to the first boundary may be smaller than a distance from the second point to the first boundary. In some embodiments, the third point may be a point on the second boundary (e.g., the point Ps in FIG. 17). In some embodiments, a distance in the vertical direction from the second point to the third point may be less than a half of the distance in the vertical direction from the start point of the edge (e.g., the point $O_f$ in FIG. 16) to the second point (e.g., the point $O_s$ in FIG. 16). In some embodiments, a distance between the start point (e.g., the point $O_f$ in FIG. 16) and the third point (e.g., the point $P_s$ in FIG. 17) in the vertical direction may be in the range from 0.5 $X_s$ to 0.9 $X_s$, where $X_s$ may be a distance in the vertical direction between the second point and the start point of the edge.

In 1150, a fourth point may be determined on a second part of the edge of the breast region based on a second slope of the line connecting the third point and the fourth point. In some embodiments, the length of the second part of the edge of the breast region may be the distance from the start point on the edge of the breast region (e.g., the point $O_f$ in FIG. 16) to another point on the edge of the breast region (e.g., the point $O_e$ in FIG. 16). In some embodiments, the length of the second part of the edge may be in a range from 0.2 $L_b$ to 0.4 $L_b$ where the $L_b$ may be a distance in the vertical direction between the start point (e.g., the point $O_f$ in FIG. 17) and an end point (e.g., the point $O_f$ in FIG. 17) on the edge of the breast region (e.g., the distance between the point $X_f$ and the point $X_e$ in FIG. 17). The slope of the line connecting the third point (e.g., the point $P_s$ in FIG. 17) and each point on the second part of the edge of the breast region (e.g., the point $O_d$, the point $O_e$, the point $P_f$ in FIG. 17) may be calculated. In some embodiments, the point corresponding to a maximum slope of the line may be selected as the fourth point (e.g., the point $P_f$ in FIG. 17).

In 1150, a target region may be determined based on the third point and the fourth point. In some embodiments, the boundary of the target region may be defined by a first line connecting the third point and the fourth point, and extending to intersect with the first boundary and the second boundary of the image. In some embodiments, the target region may be a right triangle defined by the first line, the first boundary, and the second boundary.

It should be noted that the flowchart depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the first boundary of the image may be the vertical boundary of the image. In some embodiments, the length of the first part of the edge and the second part of the edge, or a position of the third point determined based on the second point may be determined based on a statistics analysis of a plurality of image samples and the breast morphology. In some embodiments, the length the first part of the edge and the second part of the edge and/or a position of the third point may be determined to minimize the target region and to include the pectoralis sub-region. In some embodiments, the length of the first part edge and the second part edge or the position of the third point may be adjusted based on the breast morphology. In some embodiments, the target region may be a right triangle defined by the second line, the first boundary, and the second boundary of the image. The angel between the second line and the first boundary may be set by default or by an operator manually.

Figure 12:
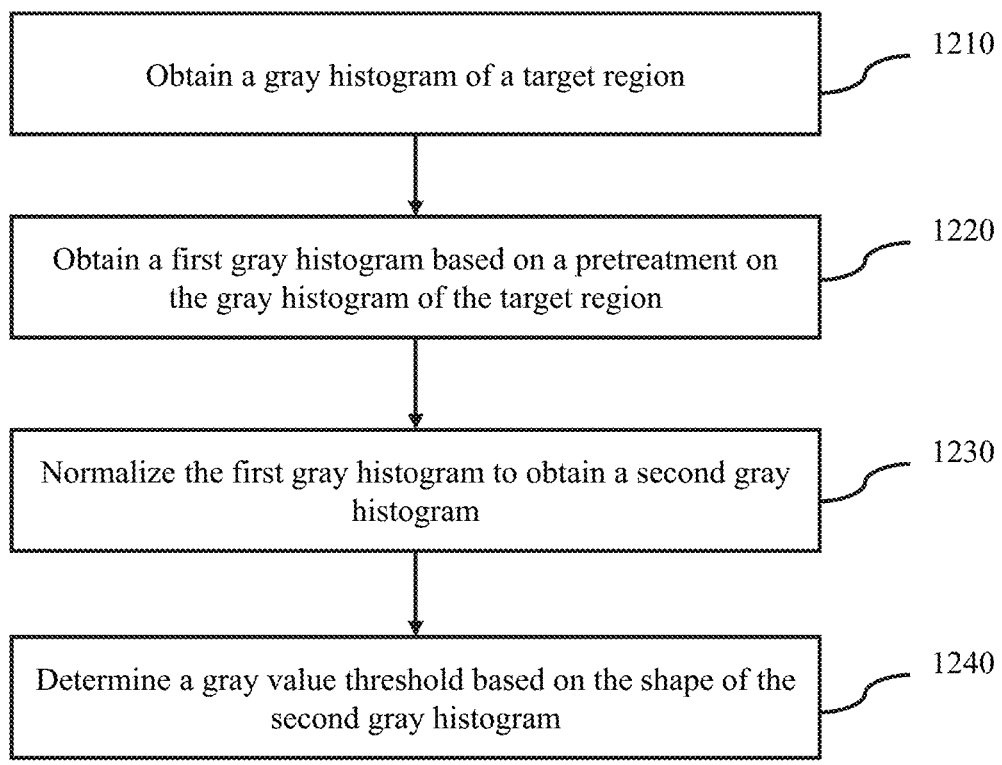
FIG. 12 is a flowchart illustrating a process 1200 for determining a gray value threshold in a target region according to some embodiments of the present disclosure.

FIG. 12 is a flowchart illustrating a process for determining a gray threshold in a target region according to some embodiments of the present disclosure. The process may be performed by the segmentation threshold determination unit 920.

In 1210, a gray value histogram of a target region may be obtained. The gray value histogram of the target region may reflect the distribution of the gray values of the pixels in the target region. In some embodiments, the X-axis of the gray value histogram may correspond to gray values, and the Y-axis of the gray value histogram may correspond to the number of pixels. In some embodiments, the Y-axis of the gray value histogram may be a frequency of pixels corresponding to a gray value. As used herein, the frequency of pixels corresponding to a gray value may be defined as a ratio of a pixel number corresponding to a gray value to a total pixel number. In some embodiments, a denoising operation may be performed on the gray value histogram to reduce noise of the gray value histogram. In some embodiments, the denoising operation may be performed using an average filter, a median filter, a Gaussian filter, bilateral filter, a normalized box filter, or the like, or a combination thereof. In some embodiments, the noise may be reduced based on a smoothing operation performed on the gray value histogram. The smoothing operation may be performed by applying a low-pass filter including, for example, an ideal circular low-pass filter, a Butterworth low-pass filter, an index low-pass filter, a trapezoid low-pass filter, or the like, or a combination thereof.

In 1220, a first gray value histogram may be obtained based on a pretreatment on the gray value histogram of the target region. The pretreatment on the gray value histogram may bring about an adjustment to the target region. The adjustment may include an increase or decrease the area of the target region, a gray value range in the gray value histogram of the target region, etc.

In some embodiments, the pretreatment on the gray value histogram may include one or more of the following operations. A total number of pixels (or a total pixel number) in the gray value histogram may be determined. A range of the gray values of the gray value histogram may be determined. An average pixel number in the gray value histogram may be determined. The average pixel number may be a ratio of the total pixel number to the gray value range in the target region. The highest gray value of the gray value histogram may be identified. A first gray threshold may be determined such that the number of pixels corresponding to the first gray threshold in the gray value histogram may be equal to or greater than the average pixel number and that the difference between the first gray threshold and the highest gray value in the gray value histogram is minimum. A region including pixels each of whose gray value is greater than the first gray value threshold may be removed from the gray value histogram.

In 1230, a second gray value histogram may be obtained by normalizing the first gray value histogram from 1220. In some embodiments, the first gray value histogram may be normalized by performing a min-max normalization or a Z-score normalization on the first gray value histogram. In some embodiments, the normalization may be performed on the pixel number corresponding to each gray value in the gray value histogram. For example, the normalization may include decreasing the pixel number corresponding to each gray value by a scale. In some embodiments, the scale may be determined based on the total pixel number in the first gray value histogram, the pixel number with the highest gray value in the first gray value histogram, etc. In some embodiments, the scale may be determined by making a maximum pixel number in the second gray value histogram equal to the difference between the greatest gray value and the gray value corresponding to the maximum pixel number in the first gray value histogram.

As another example, the normalization may include dividing the pixel number of each gray value by the total pixel number.

In 1240, a gray value threshold may be determined based on a characteristic of the second gray value histogram. In some embodiments, the characteristic of the second gray value histogram may include a shape of the second gray value histogram, a peak gray value in the second gray value histogram, a first-order derivative of the pixel numbers in the second gray value histogram, a second-order derivative of the pixel numbers in the second gray value histogram, or the like, or a combination thereof. Merely by way of example, a changing rate of the pixel numbers corresponding to different gray values in the pectoralis sub-region or one or more other sub-regions in the target region is smaller than a changing rate of the pixel numbers corresponding to different gray values in a transition region between the pectoralis sub-region and the one or more other sub-regions. Therefore, the gray value threshold may be determined based on the greatest change rate of the pixel numbers in the gray value histogram of the target region. In some embodiments, the greatest change rate of the pixel numbers may be determined based on the first-order derivative of the pixel numbers in the gray value histogram of the target region. In some embodiments, the greatest change rate may be determined based on the second-order derivative of the pixel numbers in the gray value histogram of the target region.

Figure 22:
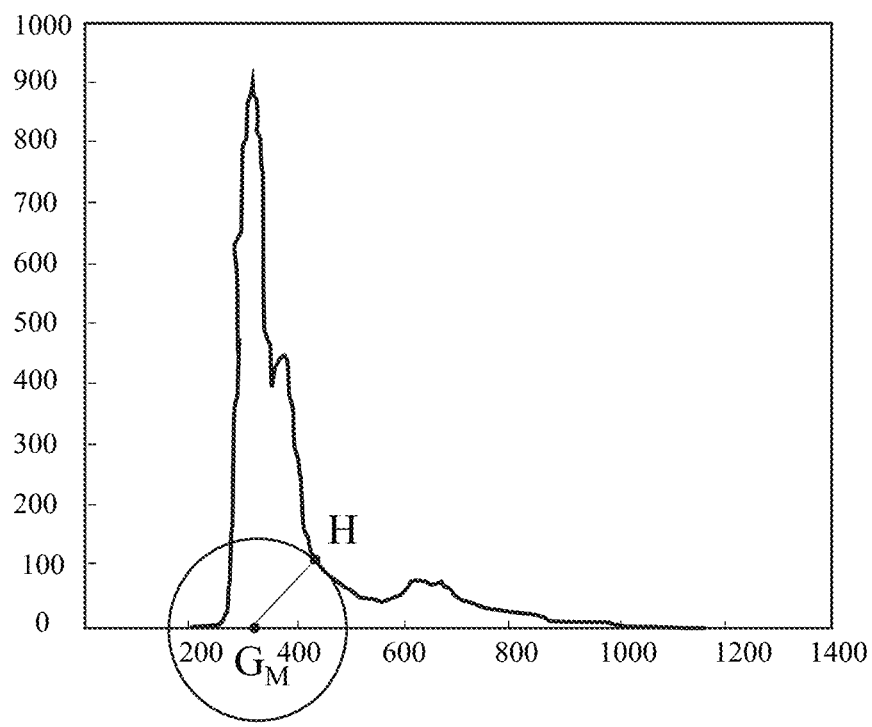
FIG. 22 is a diagram for determining a gray value threshold on a normalized gray value histogram according to some embodiments of the present disclosure.

In some embodiments, the gray value threshold may be determined based on the shape of the second gray value histogram. For illustrative purposes, as shown in FIG. 22, a gray value coordinate (herein also referred to as the point $G_M$) corresponding to the highest point or peak (i.e., the maximum pixel number) on the second gray value histogram may be identified. A point closest to any one point within a predetermined neighbourhood of the gray value coordinate corresponding to the highest point or peak (herein also referred to as the point $G_M$) may be determined on the second gray value histogram. The gray value corresponding to the point (e.g., the point H in FIG. 22) may be determined to be the gray value threshold. In some embodiments, the predetermined neighborhood may be in a range from 0 to 0.15 $G_L$, where $G_L$ may be the range of the gray value in the second gray value histogram of the target region. In some embodiments, the point corresponding to the gray value threshold may be determined based on a circle inscribing the second gray value histogram (e.g., the circle with a center of the point $G_M$ in FIG. 22). The center of the circle may be any gray value coordinate in the predetermined neighborhood. A gray value corresponding to a tangency point may be the gray value threshold.

In some embodiments, the gray value threshold may be determined based on a threshold segmentation as described elsewhere in the disclosure. For example, the gray value threshold may be determined by the Otsu's algorithm based on the second gray value histogram.

It should be noted that the flowchart depicted above is provided for the purposes of the illustration, and not intended to limit the scope of the present disclosure. For persons having ordinary skills in the art, various variations and modification may be conducted under the teaching of the present disclosure. However, those variations and modifications may not depart the scope of the present disclosure. In some embodiments, the normalization operation may be performed before the pretreatment. In some embodiments, the step 1120 may be unnecessary.

FIG. 13 is an exemplary image including a breast region according to some present disclosure. As shown in FIG. 13, a medical image relating to a breast region was generated via an FFDM system. In the medical image, the gray average value of the pixels in the first region (i.e., the top right region) may be greater than the average gray value of the pixels in the background region (i.e., the left region). The edge region lies between the first region and the background region.

Figure 14:
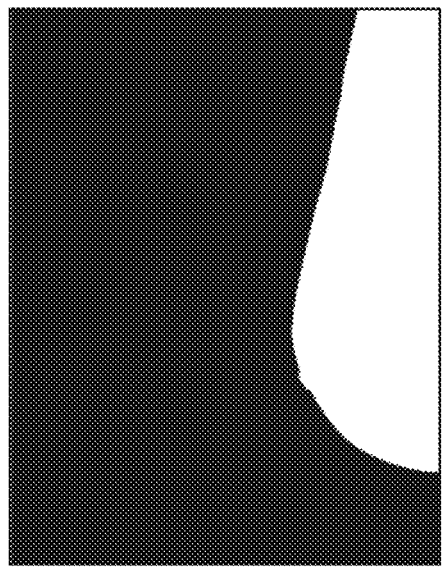
FIG. 14 is an exemplary binary image including the determined breast region according to some present disclosure.

FIG. 14 is an exemplary binary image including the determined breast region according to some present disclosure. As shown in FIG. 14, the white region (i.e., the top right region) may be the breast region including a plurality of pixels corresponding to a gray value "1." The black region (i.e., the left region) may be the background region including a plurality of pixels corresponding to a gray value "0." In the FIG. 14, the breast region and the background region may be distinguishable. A gray scale image including a breast region was obtained by multiplying the binary image including the determined breast region with a raw image (e.g., the image obtained at 510). In the breast region, the gray values corresponding to pixels in the raw image was multiplied by the gray value "1" in the binary image, and the gray values in the raw image remained the same. In the background region, the gray values corresponding to pixels in the raw image was multiplied by the gray value "0" in the binary image, and the gray values in the normal image was updated to "0."

FIGS. 15-19 are diagrams illustrating a process for determining a target region according to some embodiments of the present disclosure. As shown in FIG. 15, the image may include a horizontal boundary and a vertical boundary. The horizontal boundary was set as the Y-axis and the vertical boundary was set as the X-axis. The first point $O_f$ was determined on the horizontal boundary of the image. The first point $O_f$ was an intersection point between the horizontal boundary of the image and the edge of the breast region in the image.

As shown in FIG. 16, the second point $O_s$ was determined on the first part edge of the breast region marked in bold. The length of the first part of the edge was in a range from 0.5 $L_b$ to 0.7 $L_b$, where $L_b$ was the distance between the point $X_e$ and the point $X_f$ as shown in the image, and the point $X_e$ denoted the end point of the breast region in X-axis. The first point $O_f$ connected with one or more points on the first part of the edge of the breast region as shown in dotted lines. The slopes of the lines connecting the first point $O_f$ and the points on the first part edge of the breast region were calculated. The point $O_s$ corresponding to the minimum slope was selected to be the second point.

Figure 17:
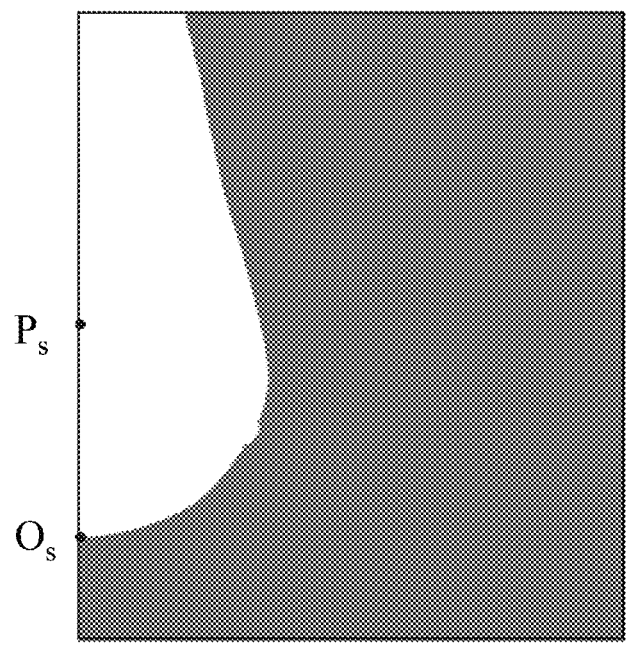

As shown in FIG. 17, the third point $P_s$ was determined on the vertical boundary of the image. The difference of X-axis coordinates between the third point $P_s$ and the second point $O_s$ was less than a half of the X-axis coordinate of the second point $O_s$. The X-axis coordinate of the third point $P_s$ was in a range from 0.5 $X_s$ o 0.9 $X_s$, where the $X_s$ was the X-axis coordinate of the second point $O_s$.

Figure 18:
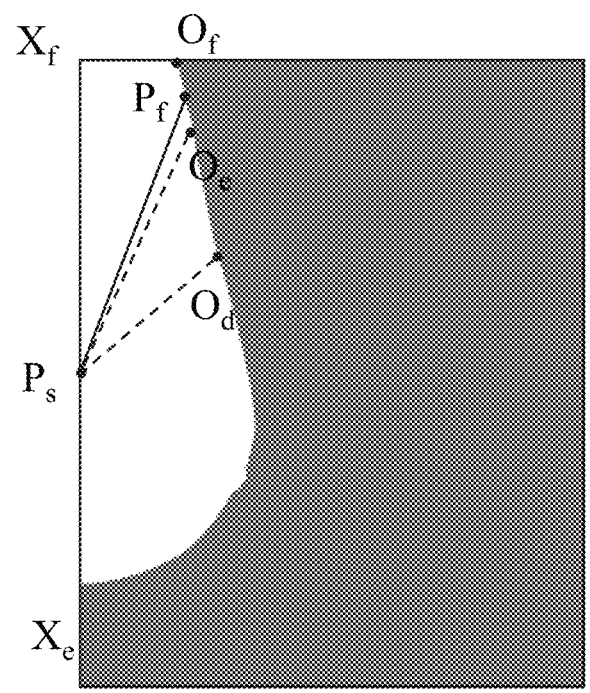

As shown in FIG. 18, the fourth point $O_f$ was determined on the second part edge of the breast region marked by the bold line. The length of the second part of the edge of the breast region in the vertical direction was in a range from 0.2 $L_b$ to 0.4 $L_b$, where $L_b$ was the distance between the point $X_e$ and the point $X_f$ as shown in the image. The fourth point connected with one or more points on the second part of the edge of the breast region as shown in dotted lines. The slopes of the lines connecting the third point $P_s$ and the points on the second part of the edge of the breast region were calculated. The point $P_f$ with the maximum slope of the line was selected to be the fourth point.

Figure 19:
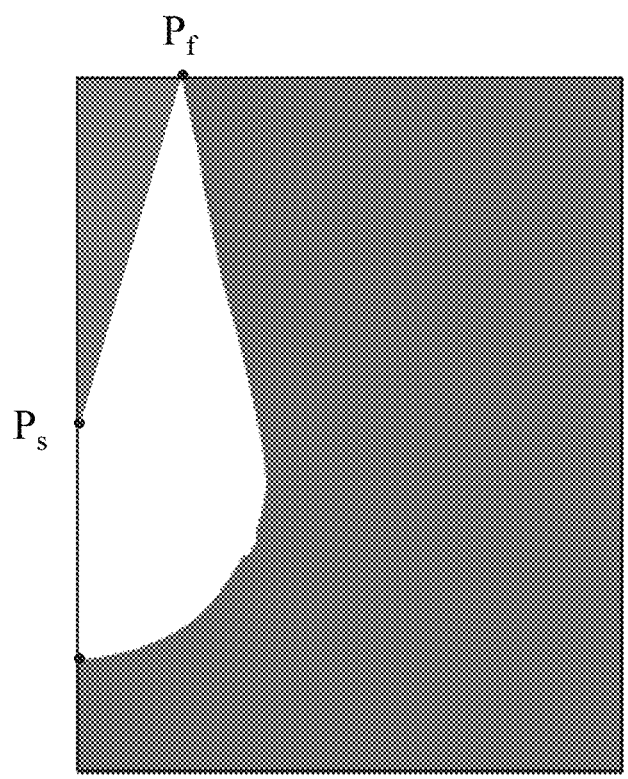

As shown in FIG. 19, the target region was a right triangle region defined by the line connecting the third point $P_s$ and the fourth point $P_f$, the horizontal boundary, and the vertical boundary of the image.

Figure 20:
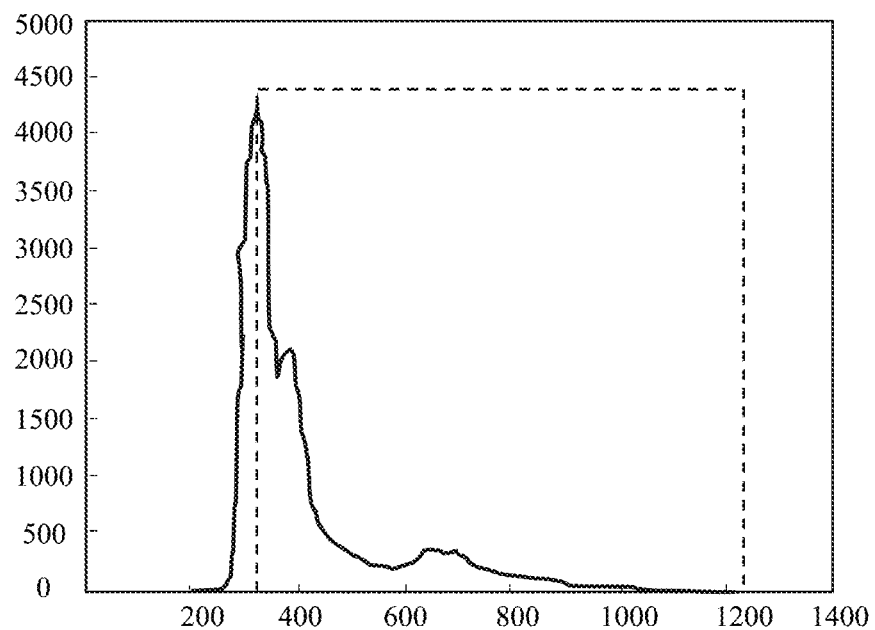
FIG. 20 is a gray value histogram of a target region according to some embodiments of the present disclosure.

FIG. 20 is a gray value histogram of a target region according to some embodiments of the present disclosure. As shown in FIG. 20, the horizontal coordinate is the gray value, and the vertical coordinate is the pixel number in the target region. A normalization operation was performed on the gray value histogram of the target region. In FIG. 20, the maximum gray value in the target region is around 1200 and the gray value corresponding to the maximum pixel number is around 300, where the maximum number of pixels is around 4500. Each coordinate value was divided by 5 such that the pixel number corresponding to the highest point or peak was equal to a difference between the maximum gray value and the gray value corresponding to the highest point or peak.

Figure 21:
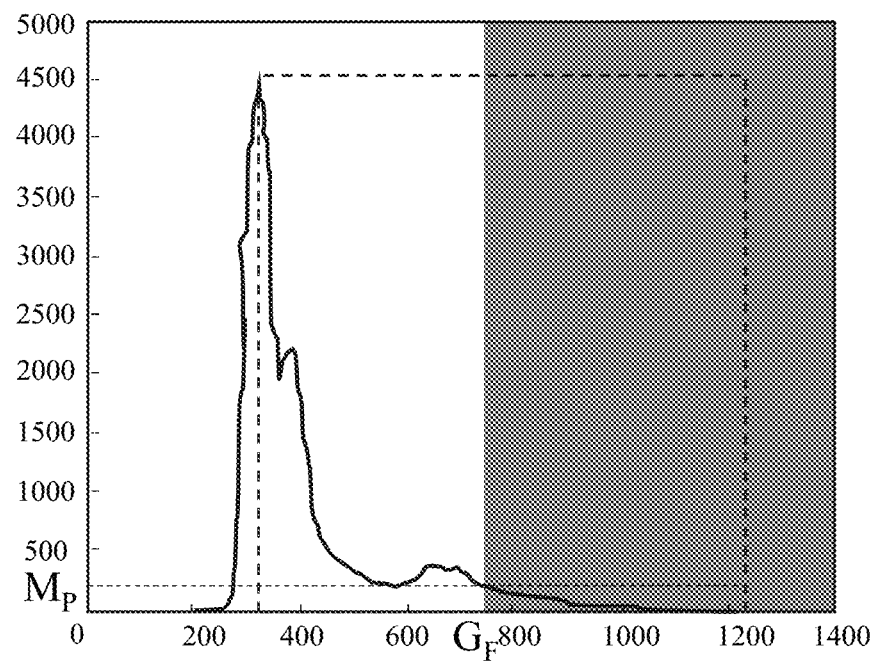
FIG. 21 is a diagram for a pretreatment on a gray value histogram according to some embodiments of the present disclosure.

FIG. 21 is a diagram for a pretreatment on a gray value histogram according to some embodiments of the present disclosure. As shown in FIG. 20, the average pixel number $M_P$ was the ratio of the total pixel number in the gray value histogram to the gray value range from 200 to around 1200. The first threshold $G_F$ was a gray value corresponding to a pixel number more than the average pixel number $M_P$ while the difference between the first threshold $G_F$ and the highest gray value aground 1200 was minimum. The region with pixels whose gray values are higher than the first threshold $G_F$ was removed, as shown in the shadow region in FIG. 20.

FIG. 22 is a diagram for determining a gray value threshold on the second gray value histogram according to some embodiments of the present disclosure. As shown in FIG. 22, the point $G_M$ was a gray value corresponding to the highest point or peak (i.e., the maximum number of pixels) in the second gray value histogram. In the second gray value histogram, a gray value of pixels in the target region was in a range from 200 to around 1200 and $G_L$ was 1000. The predetermined neighborhood was in a range from 0 to 150. As shown in FIG. 22, the predetermined neighborhood was 0, then a point closest to point $G_M$ was searched on the second gray value histogram via making a circle with a center of $G_M$. The point closest to point $G_M$ was a tangency point inscribing the second gray value histogram. The gray value threshold was the gray value corresponding to the point T on the second gray value histogram. In some embodiments, the predetermined neighborhood was determined as 150, and a nearest point apart from a gray value in the range from 300 to 450 was searched on the second gray value histogram. The center of the circle was any gray value coordinate in the predetermined neighborhood.

Figure 23:
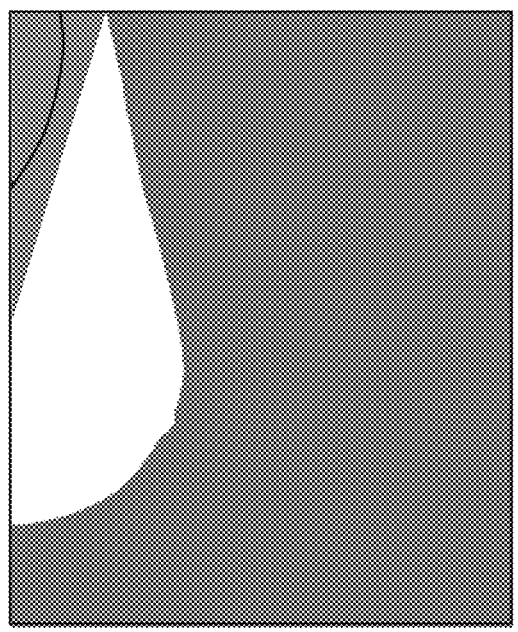
FIG. 23 is an exemplary image including a boundary of the pectoralis sub-region and a boundary of the target region according to some present disclosure.

FIG. 23 is an exemplary image including a boundary of the third region and a boundary of the target region according to some present disclosure. As shown in FIG. 23, the boundary of the third region was fitted by a quadratic term to form a parabola and the boundary of the target region was the hypotenuse of the right triangle. The boundary of the third region did not intersect with the boundary of the first region. The third region was designated as the pectoralis sub-region.

It should be noted that the above description of the embodiments are provided for the purposes of comprehending the present disclosure, and not intended to limit the scope of the present disclosure. For persons having ordinary skills in the art, various variations and modifications may be conducted in the light of the present disclosure. However, those variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one device each of which has at least one processor and at least one storage device, the method comprising:
    obtaining a first image of a subject, the first image including a first region and a second region relating to the subject, the first image including a background region, the second region relating to an edge of the subject;
    determining the first region in the first image;
    adjusting gray values of pixels in the first image to increase a difference between an average gray value of the adjusted gray values of pixels in the second region and an average gray value of the adjusted gray values of pixels in the background region;
    determining, based on the adjusted gray values of pixels in the first image, the second region; and
    determining the subject from the first image based on the first region and the second region.

2. The method of claim 1, wherein the adjusting gray values of pixels in the first image includes:
    adjusting gray values of pixels in the second region and the background region.

3. The method of claim 2, wherein the adjusting gray values of pixels in the first image further includes:
    adjusting gray values of pixels in the first region.

4. The method of claim 3, wherein a first average gray value of the adjusted gray values of the pixels in the first region is smaller than a second average gray value of the adjusted gray values of the pixels in the second region and greater than a third average gray value of the adjusted gray values of the pixels in the third region.

5. The method of claim 1, wherein the adjusting gray values of pixels in the first image includes:
    obtaining, by performing a pretreatment on the first image, a pretreated first image including the pixels with the adjusted gray values.

6. The method of claim 5, wherein the obtaining, by performing a pretreatment on the first image, a pretreated first image comprises:
    obtaining, by performing a first pretreatment on the first image, a second image; and
    obtaining, by performing a second pretreatment on the second image, the pretreated first image.

7. The method of claim 6, wherein the first pretreatment on the first image comprises a gradient transformation or a differential operation.

8. The method of claim 7, wherein the obtaining, by performing a second pretreatment on the second image, the pretreated first image comprises:
    performing a negative film operation on the first image to obtain a fourth image; and
    multiplying the second image and the fourth image to obtain the pretreated first image.

9. The method of claim 8, further comprising:
    normalizing the fourth image.

10. The method of claim 6, wherein the obtaining, by performing a first pretreatment on the first image, a second image comprises:
    denoising the first image to obtain the second image.

11. The method of claim 10, further comprising:
    performing a logarithm transformation on the first image before the denoising of the first image.

12. The method of claim 10, wherein the second pretreatment on the second image comprises a gradient transformation or a differential operation.

13. The method of claim 1, wherein the determining the second region is based on an iterative algorithm or the Otsu's algorithm.

14. The method of claim 1, further comprising:
    determining an isolated region in at least one of the first region, the second region, or the background region, the isolated region including at least one pixel corresponding to a gray value different from a circumambient pixel around the isolated region; and
    adjusting the gray value of the at least one pixel in the isolated region according to a gray value of the circumambient pixel.

15. The method of claim 1, wherein the determining the first region in the first image is based on the Otsu's algorithm.

16. The method of claim 1, further comprising:
    determining a fourth region in the first image, the fourth region including a fifth region relating to a pectoralis sub-region;
    generating a gray value histogram of the fourth region;
    determining a gray value threshold based on a characteristic of the gray value histogram; and
    determining the fifth region in the fourth region based on the gray value threshold.

17. The method of claim 16, wherein the characteristic includes at least one selected from a shape of the gray value histogram, a changing rate of pixel numbers in the gray value histogram, a peak gray value in the gray value histogram, a first-order derivative of the pixel numbers in the gray value histogram, or a second-order derivative of pixel numbers in the first gray value histogram.

18. A system, comprising:
at least one storage device storing executable instructions, and
at least one processor in communication with the at least one storage device, when executing the executable instructions, causing the system to perform operations including:
- obtaining a first image of a subject, the first image including a first region and a second region relating to the subject, the first image including a background region, the second region relating to an edge of the subject;
- determining the first region in the first image;
- adjusting gray values of pixels in the first image to increase a difference between an average gray value of the adjusted gray values of pixels in the second region and an average gray value of the adjusted gray values of pixels in the background region;
- determining, based on the adjusted gray values of pixels in the first image, the second region; and
- determining the subject from the first image based on the first region and the second region.

19. A non-transitory computer-readable storage medium embodying a computer program product, the computer program product comprising instructions configured to cause a computing device to:
- obtain a first image of a subject, the first image including a first region and a second region relating to the subject, the first image including a background region, the second region relating to an edge of the subject;
- determine the first region in the first image;
- adjust gray values of pixels in the first image to increase a difference between an average gray value of the adjusted gray values of pixels in the second region and an average gray value of the adjusted gray values of pixels in the background region;
- determine, based on the adjusted gray values of pixels in the first image, the second region; and
- determine the subject from the first image based on the first region and the second region.

* * * * *